US011415576B2

(12) United States Patent
Faatz et al.

(10) Patent No.: US 11,415,576 B2
(45) Date of Patent: Aug. 16, 2022

(54) METHOD FOR MEASUREMENT OF VITAMIN D

(71) Applicant: Roche Diagnostics Operations, Inc., Indianapolis, IN (US)

(72) Inventors: Elke Faatz, Huglfing (DE); Michael Gerg, Munich (DE); Hans-Peter Josel, Weilheim (DE); Christian Vogl, Bichl (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 285 days.

(21) Appl. No.: 15/614,856

(22) Filed: Jun. 6, 2017

(65) Prior Publication Data
US 2017/0269068 A1 Sep. 21, 2017

Related U.S. Application Data

(63) Continuation of application No. PCT/EP2015/078693, filed on Dec. 4, 2015.

(30) Foreign Application Priority Data

Dec. 8, 2014 (EP) .................................. 14196778

(51) Int. Cl.
*G01N 33/537* (2006.01)
*C07K 16/26* (2006.01)
*G01N 33/82* (2006.01)
*G01N 33/541* (2006.01)

(52) U.S. Cl.
CPC ........... *G01N 33/537* (2013.01); *C07K 16/26* (2013.01); *G01N 33/541* (2013.01); *G01N 33/82* (2013.01)

(58) Field of Classification Search
CPC .... G01N 33/537; G01N 33/82; G01N 33/541; C07K 16/26
See application file for complete search history.

(56) References Cited

U.S. PATENT DOCUMENTS

| | | | |
|---|---|---|---|
| 4,722,889 A | 2/1988 | Lee et al. | |
| 5,117,018 A * | 5/1992 | Tanabe | C07C 401/00 436/111 |
| 5,543,112 A | 8/1996 | Ghead et al. | |
| 5,641,623 A | 6/1997 | Martin | |
| 5,643,713 A | 7/1997 | Liang et al. | |
| 5,821,020 A | 10/1998 | Hollis | |
| 5,891,779 A | 4/1999 | Chung et al. | |
| 5,935,779 A | 8/1999 | Massey et al. | |
| 6,281,021 B1 | 8/2001 | Egger et al. | |
| 6,316,607 B1 | 11/2001 | Massey et al. | |
| 7,087,395 B1 | 8/2006 | Garrity et al. | |
| 2004/0132104 A1 | 7/2004 | Sackrison et al. | |
| 2013/0252342 A1 | 9/2013 | Calton et al. | |
| 2014/0147878 A1 | 5/2014 | Herman et al. | |

FOREIGN PATENT DOCUMENTS

| | | |
|---|---|---|
| CN | 201885997 U | 6/2011 |
| EP | 0500305 A2 | 8/1992 |
| EP | 0583945 A2 | 2/1994 |
| EP | 0753743 A2 | 1/1997 |
| EP | 1892524 A1 | 2/2008 |
| JP | H02-101060 A | 4/1990 |
| JP | H04-5287 A | 1/1992 |
| WO | 1987/006706 A1 | 11/1987 |
| WO | 1990/005301 A1 | 5/1990 |
| WO | 1990/005302 A1 | 5/1990 |
| WO | 1993/001308 A1 | 1/1993 |
| WO | 1998/057154 A1 | 12/1998 |
| WO | 1999/032662 A1 | 7/1999 |
| WO | 1999/058962 A1 | 11/1999 |
| WO | 1999/067211 A1 | 12/1999 |
| WO | 2001/005510 A1 | 1/2001 |
| WO | 2001/013095 A1 | 2/2001 |
| WO | 2002/057797 A2 | 7/2002 |
| WO | 2007/039194 A1 | 4/2007 |
| WO | 2011/091436 A1 | 7/2011 |
| WO | 2011/144661 A1 | 11/2011 |
| WO | WO2011144661 A1 * | 11/2011 |
| WO | 2013/072342 A1 | 5/2013 |
| WO | 2014/134139 A1 | 9/2014 |

OTHER PUBLICATIONS

Kobayashi et al. (J. Steroid Biochem. Molec. Biol. vol. 62, No. 1, pp. 79-87, published 1997). (Year: 1997).*
Roth et al. ("Accuracy and clinical implications of seven 25-hydroxyvitamin D methods compared with liquid chromatography-tandem mass spectrometry as a reference", Annals Clinical Biochemistry, vol. 45, pp. 153-159, published Mar. 2008) (Year: 2008).*
Roche Diagnostics Ltd., Elecsys® Vitamin D total assay Electrochemiluminescence binding assay (ECLIA) for the in-vitro determination of total 25-hydroxyvitamin D, 2011, 2 pp., Rotkreuz, Switzerland.
Eisman, J. A. et al., Determination of 25-Hydroxyvitamin D2 and 25-Hydroxyvitamin D3 in Human Plasma Using High-Pressure Liquid Chromatography, Analytical Biochemistry, 1977, pp. 298-305, vol. 80.
Gallo, Sina et al., Methodological issues in assessing plasma 25-hydroxyvitamin D concentration in newborn infants, Bone, 2014, pp. 186-190, vol. 61.
Guillemant, S. et al., Dosage radiocompétif simultané de la 25 hydroxyvitamine D et de la 24, 25 dihydroxyvitamine D dans le sérum humain, Annales d'Endocrinologie, 1979, pp. 75-76, vol. 40, No. 1, Paris.

(Continued)

*Primary Examiner* — Tracy Vivlemore
*Assistant Examiner* — Nam P Nguyen
(74) *Attorney, Agent, or Firm* — Stinson LLP

(57) ABSTRACT

The present invention concerns an in vitro method for measurement of 25-hydroxyvitamin D, wherein the potentially interfering compound 24,25-dihydroxyvitamin $D_3$ is blocked by a binding agent specifically binding to 24,25-dihydroxyvitamin $D_3$ and not binding to 25-hydroxyvitamin D.

14 Claims, 5 Drawing Sheets

(56) References Cited

OTHER PUBLICATIONS

Haddad, John B. and Chyu, Kyung Ja, Competitive Protein-Binding Radioassay for 25-Hydroxycholecalciferol, Journal of Clinical Endocrinology, 1971, pp. 992-995, vol. 33.

Higashi, Tatsuya et al., Enzyme-linked immunosorbent assay for plasma 24,25-dihydroxyvitamin D3, Analytica Chimica Acta, 1998, pp. 151-158, vol. 365.

Hoshino, Yu and Shea, Kenneth J., The evolution of plastic antibodies, Journal of Materials Chemistry, 2011, pp. 3517-3521, vol. 21.

International Search Report dated Feb. 8, 2016, in Application No. PCT/EP2015/078693, 4 pages.

Ong, Lizhen et al., Current 25-hydroxyvitamin D assays: Do they pass the test?, Clinica Chimica Acta, 2012, pp. 1127-1134, vol. 413.

Richter, Mark M., Electrochemiluminescence (ECL), Chemical Reviews, 2004, pp. 3003-3036, vol. 104.

Schräml, Michael and Biehl, Matthias, Kinetic Screening in the Antibody Development Process, Methods in Molecular Biology, 2012, pp. 171-181, vol. 901, Ch. 11.

Sestelo, José Pérez et al., Stereoselective Convergent Synthesis of 24,25-Dihydroxyvitamin D3 Metabolites: A Practical Approach, Chemistry—A European Journal, 2002, pp. 2747-2752, vol. 8, No. 12.

Tartarotti, D. et al., Simultaneous measurement of 1 25-dihydroxy-vitamin D, 24.25-dihydroxy-vitamin D and 25-hydroxy-vitamin D from a single two milliliters serum specimen. Preliminary clinical application, Journal of Endocrinological Investigation, 1984, pp. 545-550, vol. 7, No. 6.

Tijssen, P., Preparation of enzyme-antibody or other enzyme-macromolecule conjugates, Practice and Theory of Enzyme Immunoassays, 1990, pp. 221-278, Ch. 11, Elsevier, Amsterdam.

Zerwekh, Joseph E., The measurement of vitamin D: analytical aspects, Annual Review of Clinical Biochemistry, 2004, pp. 272-281, vol. 41.

* cited by examiner

METHOD FOR MEASUREMENT OF VITAMIN D

CROSS REFERENCE TO RELATED APPLICATIONS

This application is a continuation of International Application No. PCT/EP2015/078693 filed Dec. 4, 2015, and claims priority to European Application No. 14196778.6 filed Dec. 8, 2014, the disclosures of which are hereby incorporated by reference in their entirety.

BACKGROUND INFORMATION

The present invention concerns an in vitro method for measurement of 25-hydroxyvitamin D, wherein the potentially interfering compound 24,25-dihydroxyvitamin $D_3$ is blocked by a binding agent specifically binding to 24,25-dihydroxyvitamin $D_3$ and not binding to 25-hydroxyvitamin D.

An adequate supply of vitamin D is vital as the term "vitamin" already suggests. A deficiency of vitamin D leads to severe diseases such as rickets or osteoporosis. While vitamin D was still regarded as a single substance at the beginning of the last century, the vitamin D system has changed in the course of the last decades into a complex and manifold network of vitamin D metabolites. Nowadays more than 40 different vitamin D metabolic products are known (Zerwekh, J. E., Ann. Clin. Biochem. 41 (2004) 272-281).

Humans can only produce $D_3$ vitamins or calciferols by the action of ultraviolet rays from sunlight on the skin. In the blood Vitamin $D_3$ is bound to the so-called vitamin D-binding protein and transported to the liver where it is converted into 25-hydroxyvitamin $D_3$ by 25-hydroxylation. A multitude of other tissues are nowadays known to be involved in vitamin D metabolism in addition to the skin and liver, the two organs that have already been mentioned (Schmidt-Gayk, H. et al. (eds.), "Calcium regulating hormones, vitamin D metabolites and cyclic AMP", Springer Verlag, Heidelberg (1990) pp. 24-47). 25-hydroxyvitamin D and more specifically 25-hydroxyvitamin $D_2$ and 25-hydroxyvitamin $D_3$ are the central storage form of vitamin D in the human organism with regard to their amounts. When needed these precursors can be converted in the kidneys to form the biologically active 1α,25-dihydroxyvitamin D the so-called D hormone. The biologically active vitamin D regulates among others calcium uptake from the intestine, bone mineralization and it influences a large number of other metabolic pathways such as e.g. the insulin system.

Measuring the vitamin D level itself is of little benefit when determining the vitamin D status of a subject or patient, because concentrations of vitamin D (vitamin $D_2$ and vitamin $D_3$) fluctuate greatly depending on food uptake or exposure to sunlight. In addition vitamin D has a relatively short biological half-life in the circulation (24 hours) and it is therefore also for this reason not a suitable parameter for determining the vitamin D status of a patient. The same also applies to physiologically active forms of vitamin D (1,25-dihydroxyvitamin D). These biologically active forms also occur in relatively small and highly fluctuating concentrations compared to 25-hydroxyvitamin D. For all these reasons the quantification of 25-hydroxyvitamin D in particular is a suitable means to globally analyse the total vitamin D status of a subject or patient.

Vitamin D metabolites like 25-hydroxyvitamin D are bound with high affinity by vitamin D-binding protein and to a limited extend also to albumin and some lipoproteins. Methods appropriate to release a vitamin D metabolite from vitamin D-binding protein will under normal circumstances also be more than appropriate to release a vitamin D metabolite also from any other protein.

The binding of 25-hydroxyvitamin D or other vitamin D compounds to the vitamin D-binding protein enormously complicates the determination of vitamin D compounds. All known methods require that the vitamin D compound to be analysed is released or detached from the complex that it forms with the vitamin D-binding protein. In the following this is referred to as the release of a vitamin D compound from vitamin D-binding protein for the sake of simplification although of course it can only be released from a complex of vitamin D compound and vitamin D-binding protein and not from the vitamin D-binding protein alone.

The vitamin D-binding protein is unfolded at acidic pH, but has a high tendency to correctly refold and to re-bind the analyte when the pH is shifted back to neutral conditions. Hence, it is often necessary to firstly release vitamin D compounds from vitamin D-binding protein and then to separate the vitamin D-binding protein from the vitamin D compounds to be analysed.

Due to the high clinical importance of 25-hydroxyvitamin D a large number of methods are known from the literature which allow 25-hydroxyvitamin D to be more or less reliably determined.

Haddad, J. G. et al., J. Clin. Endocrinol. Metab. 33 (1971) 992-995, and Eisman, J. A. et al., Anal. Biochem. 80 (1977) 298-305 for example describe the determination of 25-hydroxyvitamin D concentrations in blood samples using high performance liquid chromatography (HPLC).

Other approaches for the determination of 25-hydroxyvitamin D are based among others on the use of vitamin D-binding proteins like those that are present in milk. Thus Holick, M. F. and Ray, R. (U.S. Pat. No. 5,981,779) and DeLuca et al. (EP 0 583 945) describe vitamin D assays for hydroxyvitamin D and dihydroxyvitamin D which are based on the binding of these substances to vitamin D-binding protein where the concentrations of these substances are determined by means of a competitive test procedure. However, a prerequisite of this method is that vitamin D metabolites to be determined firstly have to be isolated from the original blood or serum samples and have to be purified by, for example, chromatography.

Armbruster, F. P. et al. (WO 99/67211) teach that a serum or plasma sample should be prepared for vitamin D determination by ethanol precipitation. In this method the protein precipitate is removed by centrifugation and the ethanolic supernatant contains soluble vitamin D metabolites. These can be measured in a competitive binding assay.

Alternatively EP 0 753 743 teaches that the proteins can be separated from blood or serum samples using a periodate salt. In this case vitamin D compounds are determined in the protein-free supernatant from the samples treated with periodate. In some commercial tests acetonitrile is recommended for the extraction of serum or plasma sample (e.g. in the radioimmunoassay from DiaSorin or in the vitamin D test from the "Immundiagnostik" Company).

In recent years a number of different release reagents were proposed which should in principle be suitable for releasing vitamin D compounds from any binding protein present in the sample. However, this release or detachment should be carried out under relatively mild conditions thus enabling a direct use of the sample treated with the release reagent in a binding test (see for example WO 02/57797 and US 2004/0132104). Despite immense efforts in recent years, all available methods for determining vitamin D have disadvantages such as laborious sample preparation, poor standardization, poor agreement between test procedures or bad recovery of spiked vitamin D (see for this in particular Zerwekh, J. E., supra).

In U.S. Pat. No. 7,087,395 metal hydroxides as well as cyclodextrin and derivatives thereof, and metal salicylates have been used to release vitamin D compounds from vitamin D-binding protein, which result in an irreversible denaturation of vitamin D-binding protein or other serum proteins. Surfactants like Triton X100 or Tween-20 have been used to prevent the vitamin D compound from being non-specifically attached to lipids and proteins in the sample after denaturation.

It is particularly difficult to automate a test for a vitamin D compound. The automation requires solving a very difficult problem i.e. surviving a tightrope walk: On the one hand it is necessary to release the vitamin D compounds from vitamin D-binding protein with the aid of a suitable release reagent, on the other hand, the conditions have to be selected such that the sample can be directly analysed further. A prerequisite of this direct further analysis is that, on the one hand, the endogenous vitamin D-binding protein does not bind or no longer to a significant extent binds to the vitamin D compounds during this analysis and thus does not interfere with this analysis and, on the other hand, that the release reagent used does not interfere with the binding of detection reagents such as antibodies, or vitamin D-binding protein. In addition it is known that different alleles of the vitamin D-binding protein are present in the human population which behave biochemically differently. The release and measurement of vitamin D compounds should be comparable for various alleles/phenotypes.

Recently (WO2011/144661) a vitamin D assays that uses an appropriate sample treatment, can be performed online and without precipitation/separation of any vitamin D-binding protein that may be present in the sample. This method is based on the use of vitamin D releasing reagent containing a hydrogen carbonate salt and/or a substance capable of releasing hydrogen carbonate ions ($HCO_3^-$) upon hydrolysis in a total concentration of 0.1 M to 2.0 M, a reducing agent, and an alkalinising agent. By using this releasing reagent any vitamin D compound is released from vitamin D-binding protein, while at the same time vitamin D-binding protein comprised in the sample is inactivated and no longer binding to vitamin D. The released vitamin D compound can be measured by appropriate means.

In biological samples many vitamin D related compounds that are structurally closely related to each other are present. 24,25-dihydroxyvitamin $D_3$ is present in quite significant quantities in almost all biological samples and does interfere with the measurement of 25-hydroyvitamin D. Its concentration depends on the total amount of 25-hydroxyvitamin D in a sample as well as on the clinical background of an individual leading to variations between patient cohorts with different medicinal background. It could be shown that it is possible to avoid the interference caused by 24,25-dihydroxyvitamin $D_3$ by incubating a sample with a binding agent that binds 24,25-dihydroxyvitamin $D_3$ and does not bind to 25-hydroxyvitamin D.

SUMMARY OF THE INVENTION

In one embodiment the present invention concerns an in vitro method for determining the concentration of 25-hydroxyvitamin D without interference by 24,25-dihydroxyvitamin $D_3$, the method comprising the steps of:

a) providing a sample obtained from a subject,
b) mixing the sample
   (ba) with a first binding agent binding to 24,25-dihydroxyvitamin $D_3$, thereby forming a complex between the first binding agent and 24,25-dihydroxyvitamin $D_3$;
   (bb) with a second binding agent binding to 25-hydroxyvitamin D, thereby forming a complex between the second binding agent and 25-hydroxyvitamin D;
c) measuring the complex formed in (bb), thereby determining the concentration of 25-hydroxyvitamin D without interference by 24,25-dihydroxyvitamin $D_3$.

In a further embodiment the present invention concerns to the use of the method(s) according to the present invention for determining the concentration of 25-hydroxyvitamin D without interference by 24,25-dihydroxyvitamin $D_3$.

The present invention further is related in an embodiment to the use of a first binding agent binding to 24,25-dihydroxyvitamin $D_3$ and a second binding agent binding to 25-hydroxyvitamin D in in vitro method(s) according to the present invention for determining the concentration of 25-hydroxyvitamin D without interference by 24,25-dihydroxyvitamin $D_3$ in a sample obtained from a subject.

According to a further embodiment the present invention is related to a kit to perform the method(s) according to the present invention comprising at least
a) a first binding agent binding to 24,25-dihydroxyvitamin $D_3$, wherein the first binding agent is a monoclonal antibody or a functionally active part of the monoclonal antibody, and
b) a second binding agent binding to 25-hydroxyvitamin D, wherein the second binding agent is a vitamin D-binding protein.

DESCRIPTION OF THE FIGURES

The invention is further elucidated by the following examples and figures. The actual protective scope results from the claims attached to this invention. The embodiments are schematically depicted in the Figures.

FIG. 1 shows the chemical structure of 7-{2-[2-(2-{(S)-3-[2-[(1R,7aR)-1-((R)-4,5-Dihydroxy-1,5-dimethyl-hexyl)-7a-methyl-octahydro-inden-(4E)-ylidene]-eth-(Z)-ylidene]-4-methylene-cyclohexyloxycarbonylamino}-ethoxy)-ethoxy]-ethylcarbamoyl}-heptanoic acid N-hydroxysuccinimide ester (NHS ester of acid).

FIG. 2 shows Elecsys® Vitamin D total immunoassay without or with blocking agent (first binding agent), respectively, in reagent R1. 25-hydroxyvitamin $D_3$ (○, 25(OH)$D_3$); 24,25-dihydroxyvitamin $D_3$ (●, 24,25(OH)2D3). FIG. 2a shows results without blocking reagent (first binding agent) mAb<24,25-dihydroxyvitamin $D_3$>rK-IgG.

FIG. 2b shows results with blocking reagent (first binding agent) for interference elimination mAb<24,25-dihydroxyvitamin $D_3$>rK-IgG (mAb<24,25(OH)2D3>).

DETAILED DESCRIPTION

Figure 1:
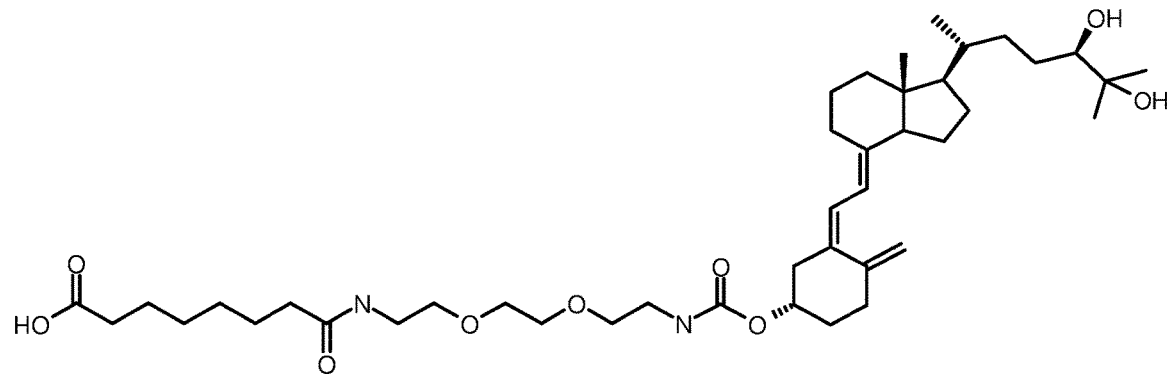
FIG. 1.

The present invention relates to a method for determining the total amount and/or concentration of 25-hydroxyvitamin D in the presence of a binding agent binding to 25-hydroxyvitamin D as well as kits, compositions and uses relating thereto.

In an embodiment the present invention concerns an in vitro method for determining the concentration of 25-hydroxyvitamin D without interference by 24,25-dihydroxyvitamin $D_3$, the method comprising the steps of:

a) providing a sample obtained from a subject,
b) mixing the sample
  (ba) with a first binding agent binding to 24,25-dihydroxyvitamin $D_3$, thereby forming a complex between the first binding agent and 24,25-dihydroxyvitamin $D_3$;
  (bb) with a second binding agent binding to 25-hydroxyvitamin D, thereby forming a complex between the second binding agent and 25-hydroxyvitamin D;
c) measuring the complex formed in (bb), thereby determining the concentration of 25-hydroxyvitamin D without interference by 24,25-dihydroxyvitamin $D_3$.

The articles "a" and "an" are used herein to refer to one or to more than one (i.e. to at least one) of the grammatical object of the article.

The expression "one or more" denotes 1 to 50, preferably 1 to 20 also preferred 2, 3, 4, 5, 6, 7, 8, 9, 10, 12, or 15.

The term "detection" refers to the qualitative or quantitative detection of an analyte in a sample to determining the amount and/or concentration of the analyte, herein measurements of an analyte such as 25-hydroxyvitamin D. "Detection" includes any means of detecting, including direct and indirect detection.

The term "determining" is used here for both qualitative and quantitative detection of an analyte in a sample, and can include determination of the amount and/or concentration of the analyte. The term also covers the identification and/or any characterization of an analyte on the basis of physical parameters.

If not stated otherwise the term "25-hydroxyvitamin D" or "vitamin D compound" is to be understood to include all naturally occurring compounds which contain the backbone of vitamin $D_2$ or the backbone of vitamin $D_3$ according to the following structural formulae I and II.

Formula I

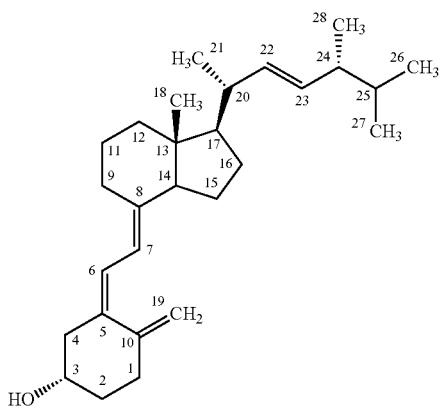

-continued

Formula II

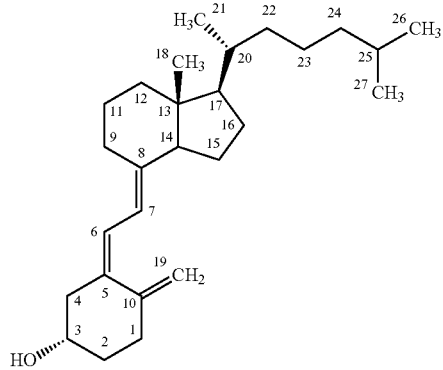

In the structural formulae I and II the positions of vitamin D are stated according to the steroid nomenclature. The 25-hydroxyvitamin D denotes vitamin D metabolites that are hydroxylated at position 25 of the structural formulae I and II i.e. the 25-hydroxyvitamin $D_2$ as well as the 25-hydroxyvitamin $D_3$. Additional known hydroxyvitamin D compounds are e.g. the 1,25-dihydroxyvitamin D and 24,25-dihydroxyvitamin D forms.

1,25-Dihydroxyvitamin D refers to the active forms of vitamin D (the so-called D hormones) that have a hydroxylation at position 1 as well as at position 25 of the structural formulae I and II.

Other well known vitamin D compounds are 24,25-dihydroxyvitamin $D_2$, 24,25-dihydroxyvitamin $D_3$ and 3-epi-25-hydroxyvitamin D.

In an embodiment according to the present invention the 25-hydroxyvitamin D is selected from the group consisting of 25-hydroxyvitamin $D_2$, 25-hydroxyvitamin $D_3$, 24,25-dihydroxyvitamin $D_2$, 24,25-dihydroxyvitamin $D_3$ and 3-epi-25-hydroxyvitamin D. In a preferred embodiment the 25-hydroxyvitamin D is selected from the group consisting of 25-hydroxyvitamin $D_2$ and 25-hydroxyvitamin $D_3$.

24,25-dihydroxyvitamin $D_3$ is present in quite significant quantities in almost allbiological samples and does interfere with the measurement of 25-hydroyvitamin D. Its concentration depends on the total amount of 25-hydroxyvitamin D in a sample as well as on the clinical background of an individual leading to variations between patient cohorts with different medicinal background. It could be shown that it is possible to avoid the interference caused by 24,25-dihydroxyvitamin $D_3$ by incubating a sample with a binding agent that binds 24,25-dihydroxyvitamin $D_3$ and does not bind to 25-hydroxyvitamin D.

If not stated otherwise the term "24,25-dihydroxyvitamin D" is to be understood to include all naturally occurring compounds which contain the backbone of vitamin $D_3$ and a OH group at carbon atom 24 and 25, respectively, according to the following structural formula III. In an embodiment according to the present invention the 24,25-dihydroxyvitamin D is 24,25-dihydroxyvitamin $D_3$ (24(R),25-(OH)$_2D_3$).

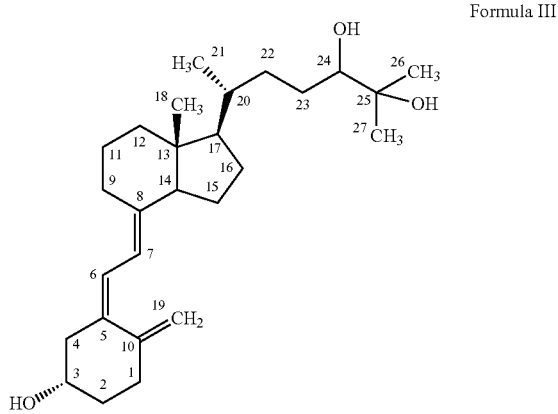 [SMILES: C=C1CC[C@H](O)C/C1=C/C=C1\CCC[C@@]2(C)C1CC[C@@H]2[C@H](C)CCC(O)C(C)(C)O]

Formula III

The sample which comprises the analyte(s) (e.g. 25-hydroxyvitamin D, 24,25-dihydroxyvitamin $D_3$) may be a liquid, gel or liquefiable composition, preferably a liquid. Such liquid may be a solution, suspension or emulsion. In particular, the sample is a biological sample, in particular a bodily sample obtained from a human or animal, or mixtures thereof. Such bodily sample may be used directly after retrieval from a subject, or may be stored under adequate conditions, e.g. by freezing, in order to perform the method of the invention at a intended point of time. In particular, samples from various subjects and/or different time points may be measured in order to compare subjects or to monitor a therapy. The retrieval of a bodily sample may be performed by a skilled person depending on the sample. In a preferred embodiment, the sample is blood, serum or plasma. In a yet further embodiment, the sample is blood or blood serum. In such case, blood is taken from a subject. Blood serum may be obtained from blood by methods known in the art. Similarly, other bodily samples may be obtained by e.g. collecting urine, or by taking a biopsy, and by further treatment of the sample, if necessary.

As described above, the sample comprises the analyte(s) 25-hydroxyvitamin D and 24,25-dihydroxyvitamin $D_3$, respectively.

"Binding pair member" refers to a member of a binding pair ("bp"), which means two different molecules wherein one of the molecules binds with the second molecule through chemical or physical means. In addition to the antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence or chemical moiety (such as digoxin/anti-digoxin) and an antibody specific for the sequence, chemical moiety or the entire protein, polymeric acids and bases, dyes and corresponding protein binders, peptides and specific protein binders (e.g., ribonuclease, S-peptide and ribonuclease S-protein), metals and their chelators, aptamers, and the like. Furthermore, binding pairs can include a member that is an analog of an original binding member, for example an analyte-analog or e.g. a binding member made by recombinant techniques or molecular engineering that is analogous to the original binding pair member and has the same binding properties.

A binding pair member is analogous to a binding pair member if they are both capable of binding to the complementary member of the binding pair with the same way. Such binding pair member may, for example, be either a ligand or a receptor that has been modified by the replacement of at least one hydrogen atom by a group to provide, for example, a labeled ligand or labeled receptor. The binding pair members can be analogous to the analyte or to the binding pair member that is complementary to the analyte.

A "binding agent" is a member of a binding pair ("bp") that binds to the other member of the binding pair, the corresponding target molecule, e.g. 24,25-dihydroxyvitamin $D_3$. The affinity ($K_d$) of a binding agent is $10^{-7}$ mol/L for its corresponding target molecule. A binding agent has preferably an affinity of $10^{-8}$ mol/L. Further preferred a binding agent has an affinity of $10^{-9}$ mol/L for its target molecule. Even more preferred a binding agent has an affinity of $10^{-10}$ mol/L for its target molecule.

As the skilled artisan will appreciate the term "first binding agent" binding to 24,25-dihydroxyvitamin $D_3$ is used to indicate that other biomolecules present in the sample do not significantly bind to the binding agent specific for 24,25-dihydroxyvitamin $D_3$. Preferably, the level of binding of the specific binding agent to a biomolecule other than the target molecule results in a binding affinity which is only 10% or less, preferably only 5% or less, respectively, of the affinity to the target molecule. A preferred first binding agent binding to 24,25-dihydroxyvitamin $D_3$ will fulfill both the above minimum criteria for affinity as well as for specificity.

A "first binding agent" according to the present invention is in an embodiment selected from the group consisting of polyclonal antibody, monoclonal antibody and synthetic antibody (plastic antibody), preferred a monoclonal antibody or synthetic antibody, further preferred a monoclonal antibody or a functionally active part of the monoclonal antibody, respectively. The first binding agent is binding in an embodiment to 24,25-dihydroxyvitamin D, further preferred the first binding agent is binding 24,25-dihydroxyvitamin $D_3$. Preferably the antibody is a monoclonal antibody binding to 24,25-dihydroxyvitamin $D_3$. Further preferred the antibody is a plastic antibody binding to 24,25-dihydroxyvitamin $D_3$.

A "plastic antibody" according to the present invention is a synthetic polymer nanoparticle with an antibody-like function (Hoshino, Y. et al., J. Mater. Chem., 2011, 21, 3517-3521). A plastic antibody according to the present invention is capable of binding and neutralizing specific 24,25-dihydroxyvitamin $D_3$.

A "second binding agent" according to the present invention is in an embodiment a vitamin D-binding protein (VitD-BP) or a antibody or a functionally active part of the antibody, binding to 25-hydroxyvitamin D. Further preferred the second binding agent is a vitamin D-binding protein, preferred a recombinant vitamin D-binding protein. In a yet further embodiment the second binding agent is a functionally active part of the vitamin D-binding protein, preferably domain I of the vitamin D-binding protein.

In the Examples of the present invention, the antibody mAb<24,25-dihydroxyvitamin $D_3$>rK-IgG was used successfully as first binding agent. In a preferred embodiment the first binding agent is mAb<24,25-dihydroxyvitamin $D_3$>rK-IgG.

Naturally occurring antibodies are globular plasma proteins (~150 kDa (http://en.wikipedia.org/wiki/Dalton_unit)) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. In the present invention, examples of suitable formats include the format of naturally occurring antibodies including antibody isotypes known as IgA, IgD, IgE, IgG and IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two beta sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals. Other types of light chains, such as the t chain, are found in lower vertebrates like Chondrichthyes and Teleostei.

In addition to naturally occurring antibodies, artificial antibody formats including antibody fragments have been developed. Some of them are described in the following.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

Accordingly, the term "antibody", as used herein, means any polypeptide which has structural similarity to a naturally occurring antibody and is capable of specific binding to the respective target, wherein the binding specificity is determined by the CDRs. Hence, "antibody" is intended to relate to an immunoglobulin-derived structure with binding to the respective target including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to the respective target. The antibody or functionally active parts thereof may be any polypeptide which comprises at least one antigen binding fragment. Antigen binding fragments consist of at least the variable domain of the heavy chain and the variable domain of the light chain, arranged in a manner that both domains together are able to bind to the specific antigen. The "respective target" is the analyte in case of the capture molecule, the binding molecule and the detection molecule, and is the binding molecule in case of the anti-idiotype antibody as preferred trapping molecule.

"Full length" or "complete" antibodies refer to proteins that comprise two heavy (H) and two light (L) chains inter-connected by disulfide bonds which comprise: (1) in terms of the heavy chains, a variable region and a heavy chain constant region which comprises three domains, CH1, CH2 and CH3; and (2) in terms of the light chains, a light chain variable region and a light chain constant region which comprises one domain, CL. With regard to the term "complete antibody", any antibody is meant that has a typical overall domain structure of a naturally occurring antibody (i.e. comprising a heavy chain of three or four constant domains and a light chain of one constant domain as well as the respective variable domains), even though each domain may comprise further modifications, such as mutations, deletions, or insertions, which do not change the overall domain structure.

"Functionally active parts of antibodies" or "antibody fragments" also contain at least one antigen binding fragment as defined above, and exhibit essentially the same function and binding specificity as the complete antibody of which the functionally active part (or fragment) is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

As the first generation of full sized antibodies presented some problems, many of the second generation antibodies comprise only fragments of the antibody. Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment, which is a preferred functionally active part of an antibody according to the invention. In general, it has a high affinity for its antigen and can be expressed in a variety of hosts. These and other properties make scFv fragments not only applicable in medicine, but also of potential for biotechnological applications. As detailed above, in the scFv fragment the VH and VL domains are joined with a hydrophilic and flexible peptide linker, which improves expression and folding efficiency. Usually linkers of about 15 amino acids are used, of which the (Gly4Ser)3 linker has been used most frequently. scFv molecules might be easily proteolytically degraded, depending on the linker used. With the development of genetic engineering techniques these limitations could be practically overcome by research focused on improvement of function and stability. An example is the generation of disulfide-stabilized (or disulfide-linked) Fv fragments where the VH-VL dimer is stabilized by an interchain disulfide bond. Cysteines are introduced at the interface between the VL and VH domains, forming a disulfide bridge, which holds the two domains together.

Dissociation of scFvs results in monomeric scFvs, which can be complexed into dimers (diabodies), trimers (triabodies) or larger aggregates such as TandAbs and Flexibodies, which also represent functionally active parts of an antibody according to the invention.

Antibodies with two binding domains can be created either through the binding of two scFv with a simple polypeptide link (scFv)2 or through the dimerization of two monomers (diabodies). The simplest designs are diabodies that have two functional antigen-binding domains that can be either the same, similar (bivalent diabodies) or have specificity for distinct antigens (bispecific diabodies). These bispecific antibodies allow for example the recruitment of novel effector functions (such as cytotoxic T cells) to the target cells, which make them very useful for applications in medicine.

Also, antibody formats comprising four variable domains of heavy chains and four variable domains of light chains have been developed. Examples of these include tetravalent bispecific antibodies (TandAbs and Flexibodies, Affimed Therapeutics AG, Heidelberg. Germany). In contrast to a bispecific diabody, a bispecific TandAb is a homodimer consisting of only one polypeptide. Because the two different chains, a diabody can build three different dimers only one of which is functional. Therefore, it is simpler and cheaper to produce and purify this homogeneous product. Moreover, the TandAb usually shows better binding properties (possessing twice the number of binding sites) and increased stability in vivo. Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multispecific.

In summary, specific immunoglobulin types which represent antibodies or functionally active parts thereof include but are not limited to the following antibody: a Fab (monovalent fragment with variable light (VL), variable heavy (VH), constant light (CL) and constant heavy 1 (CH1) domains), a F(ab')2 (bivalent fragment comprising two Fab fragments linked by a disulfide bridge or alternative at the hinge region), a Fv (VL and VH domains), a scFv (a single chain Fv where VL and VH are joined by a linker, e.g., a peptide linker), a bispecific antibody molecule (an antibody molecule with specificity as described herein linked to a second functional moiety having a different binding specificity than the antibody, including, without limitation, another peptide or protein such as an antibody, or receptor ligand), a bispecific single chain Fv dimer, a diabody, a triabody, a tetrabody, a minibody (a scFv joined to a CH3).

Certain antibody molecules or functionally active parts thereof including, but not limited to, Fv, scFv, diabody molecules or domain antibodies (Domantis) may be stabilized by incorporating disulfide bridges to line the VH and VL domains. Bispecific antibodies may be produced using conventional technologies, specific methods of which include production chemically, or from hybrid hybridomas) and other technologies including, but not limited to, the BiTETM technology (molecules possessing antigen binding regions of different specificity with a peptide linker) and knobs-into-holes engineering.

Accordingly, an antibody molecule or functionally active part thereof may be a Fab, a Fab', a F(ab')2, a Fv, a disulfide-linked Fv, a scFv, a (scFv)2, a bivalent antibody, a bispecific antibody, a multispecific antibody, a diabody, a triabody, a tetrabody or a minibody.

In another preferred embodiment, the antibody is a monoclonal antibody, a chimeric antibody or a humanised antibody. Monoclonal antibodies are monospecific antibodies that are identical because they are produced by one type of immune cell that are all clones of a single parent cell. A chimeric antibody is an antibody in which at least one region of an immunoglobulin of one species is fused to another region of an immunoglobulin of another species by genetic engineering in order to reduce its immunogenicity. For example murine VL and VH regions may be fused to the remaining part of a human immunoglobulin. A particular type of chimeric antibodies are humanised antibodies. Humanised antibodies are produced by merging the DNA that encodes the CDRs of a non-human antibody with human antibody-producing DNA. The resulting DNA construct can then be used to express and produce antibodies that are usually not as immunogenic as the non-human parenteral antibody or as a chimeric antibody, since merely the CDRs are non-human.

In a preferred embodiment of the present invention, an antibody molecule or functionally active part thereof used in a method of the invention comprises a heavy chain immunoglobulin constant domain selected from the group consisting of: a human IgM constant domain, a human IgG1 constant domain, a human IgG2 constant domain, a human IgG3 constant domain, a human IgG4 constant domain, a human IgE constant domain, and a human IgA constant domain.

As detailed above in the context with the antibody of the present invention, each heavy chain of a naturally occurring antibody has two regions, the constant region and the variable region. There are five types of mammalian immunoglobulin heavy chain: $\gamma$, $\delta$, $\alpha$, $\mu$ and $\varepsilon$, which define classes of immunoglobulins IgM, IgD, IgG, IgA and IgE, respectively.

There are here are four IgG subclasses (IgG1, 2, 3 and 4) in humans, named in order of their abundance in serum (IgG1 being the most abundant). Even though there is about 95% similarity between their Fc regions of the IgG subclasses, the structure of the hinge regions are relatively different. This region, between the Fab arms (Fragment antigen binding) and the two carboxy-terminal domains CH2 and CH3 of both heavy chains, determines the flexibility of the molecule. The upper hinge (towards the amino-terminal) segment allows variability of the angle between the Fab arms (Fab-Fab flexibility) as well as rotational flexibility of each individual Fab. The flexibility of the lower hinge region (towards the carboxy-terminal) directly determines the position of the Fab-arms relative to the Fc region (Fab-Fc flexibility). Hinge-dependent Fab-Fab and Fab-Fc flexibility may be important in triggering further effector functions such as complement activation and Fc receptor binding. Accordingly, the structure of the hinge regions gives each of the four IgG classes their unique biological profile.

The length and flexibility of the hinge region varies among the IgG subclasses. The hinge region of IgG1 encompasses amino acids 216-231 and since it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, it is relatively short and contains a rigid poly-proline double helix, stabilised by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3 the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2.

In case a vitamin D-binding protein is used as a second binding agent, the pH during this incubation step is in an embodiment preferably selected between pH 6.0 and pH 9.0.

In case an antibody binding 25-hydroxyvitamin D is used in an embodiment as a second binding agent, the pH during this incubation step will be between pH 5 and pH 8, preferably the pH during this incubation step will be between pH 5.5 and pH 7.5.

According to a specific embodiment the first binding agent is a monoclonal antibody or a functionally active part of the monoclonal antibody, and the second binding agent is a vitamin D-binding protein or a functionally active part of the vitamin D-binding protein.

In a further embodiment the first binding agent is a monoclonal antibody or a functionally active part of the monoclonal antibody and the second binding agent is a monoclonal antibody or a functionally active part of the monoclonal antibody.

Also in a further embodiment the first binding agent is mAb<24,25-dihydroxyvitamin $D_3$> or a functionally active part of the monoclonal antibody and the second binding agent is mAb<25-hydroxyvitamin D> or a functionally active part of the monoclonal antibody.

In an embodiment according to the present invention, a binding agent carries means for immobilization and can be used for immobilization. The means for immobilization may allow binding to a support, preferably solid support, covalently or non-covalently.

The term "solid support" or "solid phase" refers to a material in the solid-phase that interacts with reagents in the liquid phase by heterogeneous reactions. The use of solid supports is well known in the fields of chemistry, biochemistry, pharmacy and molecular biology. Many types of solid supports have been developed depending on the technical problem to be solved. Any of these may be used in the context of the present invention. For example, the solid support used in the methods of the present invention may include components of silica, cellulose acetate, nitrocellulose, nylon, polyester, polyethersulfone, polyolefin, or polyvinylidene fluoride, or combinations thereof. Further suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

Common resin supports used e.g. in combinatorial or protein chemistry include polystyrene resin, e.g. cross-linked with divinylbenzene; hydroxymethylpolystyrene; aminomethylpolystyrene; TentaGel resin (TG) and ArgoGel (AG): polystyrene/DVB-poly(ethylene glycol) graft copolymers (PS-PEG)—Bayer; Crowns/Pins (CP) (radiation-grafted polyethylene/polypropylene support); Kieselguhr/polyacrylamide-based resins (KPA); Controlled-pore glass; PEGA—poly(ethylene glycol)/dimethylacrylamide copolymer.

Immobilization to a solid support may be accomplished using solid supports that have been modified or activated to include functional groups that permit the covalent coupling of the entity or support to the binding agent, e.g. a protein or a antibody. Typically, aliphatic linker arms are employed. The binding agent, particularly proteins or antibodies, can also be noncovalently attached to a surface, through, for example, ionic or hydrophobic mechanisms, and are detached by the releaser inhibiting these mechanisms locally. Additionally, covalent attachment of a bindin agent, e.g. a protein or antibody, to a surface, e.g. a glass or metal oxide surface, can be accomplished by first activating the surface with an amino silane. Binding agents derivatized with amine-reactive functional groups can then attach to the surface. Supports, in particular solid supports can be derivatized with proteins such as enzymes, peptides, oligonucleotides and polynucleotides by covalent or non-covalent bonding through one or more attachment sites, thereby binding the same acid to the solid support.

The (solid) support may be contained in a vessel, wherein the vessel is a tube, such as a centrifuge tube or spin tube, syringes, cartridge, chamber, multiple-well plate, or test tube, or combinations thereof. The (solid) support may be pre-treated or functionalized in order to allow linker-mediated binding of the binding agent. In one embodiment, the solid support may be fibrous or particulate usually allowing for appropriate contacting. The size of the (solid) support suitable for use in the method of this invention may vary according to method chosen. The first binding agent or second binding agent, respectively, may be bound to one (solid) support only (e.g. one vessel or multi-well plate) or may be bound to a multitude of (solid) supports (e.g. beads). The shape of the (solid) support suitable for use in the methods of this invention may be, for example, a sheet, a precut disk, cylinder, single fiber, or a solid support composed of particulates. In one embodiment, the (solid) support may be fibrous or particulate to allow optimal contacting. The size of the (solid) support may vary and may be chosen depending from the method to be carried out.

In some embodiments, the solid support is a test strip, a chip, in particular a microarray or nanoarray chip, a microtiter-plate or a microparticle (bead).

Many commercial test systems are based on the use of solid support coated with avidin or streptavidin (SA), for example SA-coated microtitre plates, SA-coated lattices, or SA-coated microparticles (beads).

A biotinylated analyte derivative is for example bound to this SA solid support before or during the test procedure. When detecting vitamin D compound this biotinylated analyte derivative compound can for example be a biotinylated 25-hydroxyvitamin $D_2$ and/or a biotinylated 25-hydroxyvitamin $D_3$.

In one embodiment of the present invention the in vitro method of detection is carried out as a competitive assay. In such a competitive test a derivative of vitamin D compound added in a defined amount to the test competes with the corresponding vitamin D compound from the sample for the binding sites of the specific binding agent. The more vitamin D compound is present in the sample, the smaller is the detection signal.

In one embodiment the derivative of a vitamin D compound is a biotinylated vitamin D compound. In a further embodiment the biotinylated vitamin D compound is a biotinylated 25-hydroxyvitamin $D_2$ and/or biotinylated 25-hydroxyvitamin $D_3$. In a further embodiment the biotinylated vitamin D compound is a biotinylated 25-hydroxyvitamin $D_2$.

In one embodiment the derivative of a vitamin D compound is a ruthenylated vitamin D compound. In a further embodiment the ruthenylated vitamin D compound is a ruthenylated 25-hydroxyvitamin $D_2$ and/or ruthenylated 25-hydroxyvitamin $D_3$. In a further embodiment the ruthenylated vitamin D compound is a ruthenyated 25-hydroxyvitamin $D_2$.

As mentioned above preferred second binding agents for use in a detection method as disclosed in the present description are antibodies and vitamin D-binding protein. Vitamin D-binding protein, if used in a competitive assay format, will lead to an integrated measurement of all vitamin D compounds competing with its binding to one ore more (biotinylated) vitamin D compound derivative. In one embodiment the vitamin D-binding protein will be detectable labeled, e.g. ruthenylated.

In an embodiment the method according to the present invention is performed in a competitive assay format, wherein
  i) the solid support is a SA-coated microparticle (bead), the competitor is a derivative of a biotinylated vitamin D compound and the second binding agent is a ruthenylated vitamin D-binding protein conjugate, or
  ii) the solid support is a SA-coated microparticle (bead), the competitor is a ruthenylated vitamin D conjugate and the second binding agent is biotinylated vitamin D-binding protein conjugate.

According to a preferred embodiment, the first binding agent prevents binding of 24,25-dihydroxyvitamin $D_3$ to the second binding agent. In a yet further preferred embodiment the 24,25-dihydroxyvitamin $D_3$ bound to the first binding agent cannot be bound by the second binding agent. Also in a further embodiment the second binding agent is not capable of releasing the 24,25-dihydroxyvitamin $D_3$ bound to the first binding agent.

A person skilled in the art is aware, that a vitamin D compound present in a sample obtained from a subject is bound to vitamin D-binding protein. Therefore in the methods according to the present invention the vitamin D compound present in the sample bound to vitamin D-binding protein is released from vitamin D-binding protein prior to step (b) with a release reagent in a specific embodiment.

The provided sample obtained from a subject according to the methods comprises a vitamin D compound bound to vitamin D-binding protein in an embodiment.

A release reagent denaturates the vitamin D-binding protein, preferably the release reagent irreversible denaturates the vitamin D-binding protein.

In an specific embodiment the vitamin D compound is released from the vitamin D-binding protein prior to step (b) by a method selected from the group consisting of a proteolytic degradation, an acidic release, an alkaline release, a methanol release, an ethanol precipitation (WO 99/67211), a periodate salt release (EP 0 753 743), an acetonitrile extraction, a metal hydroxide release (U.S. Pat. No. 7,087, 395), a release by cyclodextrin and/or derivatives thereof (U.S. Pat. No. 7,087,395) or a metal salicylate release (U.S. Pat. No. 7,087,395), respectively. The person skilled in the art is aware of methods suitable to release a vitamin D compound bound to vitamin D-binding protein prior to the determination/measurement of the vitamin D compound. In recent years a number of different release reagents were proposed which should in principle be suitable for releasing vitamin D compounds from any binding protein present in the sample.

In a further embodiment the present invention concerns an in vitro method for determining the concentration of 25-hydroxyvitamin D without interference by 24,25-dihydroxyvitamin $D_3$, the method comprising the steps of:
  a) providing a sample obtained from a subject and releasing the vitamin D compound present in the sample bound to vitamin D-binding protein with a release reagent,
  b) mixing the sample
    (ba) with a first binding agent binding to 24,25-dihydroxyvitamin $D_3$, thereby forming a complex between the first binding agent and 24,25-dihydroxyvitamin $D_3$;
    (bb) with a second binding agent binding to 25-hydroxyvitamin D, thereby forming a complex between the second binding agent and 25-hydroxyvitamin D;
  c) measuring the complex formed in (bb), thereby determining the concentration of 25-hydroxyvitamin D without interference by 24,25-dihydroxyvitamin $D_3$.

According to a specific embodiment the vitamin D compound is released from the vitamin D-binding protein prior to step (b) by an alkaline release. Alkaline conditions result in the denaturation of vitamin D-binding protein and release of vitamin D compound present in the sample to be investigated. The concentration of the alkalinising agent has to be sufficient to increase the pH of the "reagent mixture" (=a sample to be investigated+alkalinising agent+additional reagents) to at least pH 10.0, preferably to at least pH 10.5, more preferably to at least 11.0 in the pre-treatment reaction prior to step (b). The skilled artisan is aware, that the pH of the reagent mixture has to be measured at the time of mixture of the sample to be investigated+alkalinising agent+ additional reagents. Due to the hydrolysis of the hydrogen carbonate salt and/or the substance capable of releasing hydrogen carbonate ions ($HCO_3^-$) upon hydrolysis, the pH will be reduced in the reagent mixture.

The release reagent comprises in a specific embodiment a hydrogen carbonate salt and/or a substance capable of releasing hydrogen carbonate ions ($HCO_3^-$) upon hydrolysis in a concentration of 0.1 M to 2.0 M, a reducing agent and an alkalinising agent. In a further specific embodiment the release reagent comprises a hydrogen carbonate salt in a concentration of 0.1 M to 2.0 M, a reducing agent and an alkalinising agent. In a further specific embodiment the release reagent comprises a substance capable of releasing hydrogen carbonate ions ($HCO_3^-$) upon hydrolysis in a concentration of 0.1 M to 2.0 M, a reducing agent and an alkalinising agent. Such release reagents and release methods are described in detail in WO 2011/144661 and WO 2013/072342.

A "hydrogen carbonate ion" (bicarbonate ion) is an anion with the empirical formula $HCO_3^-$ and a molecular mass of 61.01 daltons.

A "hydrogen carbonate salt" is a compound selected from the group consisting of sodium hydrogen carbonate ($NaHCO_3$), potassium hydrogen carbonate ($KHCO_3$), ammonium hydrogen carbonate ($NH_4HCO_3$), calcium hydrogene carbonate ($Ca(HCO_3)_2$) and magnesium hydrogen carbonate ($Mg(HCO_3)_2$).

A "substance capable of releasing hydrogen carbonate ions ($HCO_3^-$) upon hydrolysis" according to an embodiment of the present invention is a carbonate ester. A "carbonate ester" according to the present invention is a carbonyl group flanked by two alkoxy groups. The general structure of these carbonates is $R_1O(C=O)OR_2$. There are cyclic carbonate esters (e.g. ethylene carbonate) or non-cyclic carbonate esters (e.g. dimethyl carbonate) as well as hydroxylated or halogenized derivatives thereof available.

A person skilled in the art is aware to select a suitable reducing agent, e.g. selected from the group consisting of 2-Mercaptoethanol, 2-Mercaptoethylamine-HCl, TCEP, Cystein-HCl and Dithiothreitol (DTT).

Also the skilled person is aware to select suitable alkalinising agents, e.g. selected from the group consisting of NaOH, KOH, $Ca(OH)_2$ and LiOH, or a mixture thereof.

It is advantageous if essentially complete release of the analyte (Vitamin D compound) from the binding molecule (Vitamin D-binding protein) is made prior the step (b) of the methods according to the present invention.

In step (b) of the methods according to the present invention, the first binding agent and the second binding agent are contacted simultaneously with the sample in a specific embodiment. In other words, in a specific embodiment the steps (ba) and (bb) are performed simultaneously according to the method(s) of the present invention.

In step (b) of the methods according to the present invention the first binding agent is contacted with the sample before or after contacting the second binding agent with the sample in a specific embodiment. In other words, in a specific embodiment the step (ba) is performed before step (bb) according to the method(s) of the present invention. In a further embodiment the step (ba) is performed after step (bb) according to the method(s) of the present invention.

In an embodiment according to the method of the present invention the concentration of 25-hydroxyvitamin D is determined/measured/detected in an immunoassay procedure.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates, In: Practice and theory of enzyme immunoassays, pp. 221-278, Burdon, R. H. and v. Knippenberg, P. H. (eds.), Elsevier, Amsterdam (1990), and various volumes of Methods in Enzymology, Colowick, S. P., and Caplan, N. O. (eds.), Academic Press), dealing with immunological detection methods, especially volumes 70, 73, 74, 84, 92 and 121.

In an embodiment the method for determining the concentration of 25-hydroxyvitamin D is selected from the group consisting of an enzyme-linked immunoassay (ELISA), electrochemiluminescence immunoassay (ECLIA), radioimmunoassay (RIA) and chemiluminescent immunoassay (CLIA). In a preferred embodiment 25-hydroxyvitamin D is detected in an enzyme-linked immunoassay (ELISA). 25-hydroxyvitamin D is detected in a further preferred embodiment in an (electro-) chemiluminescence immunoassay (ECLIA). 25-hydroxyvitamin D is detected in a further embodiment in a radioimmunoassay (RIA). Also a preferred embodiment is a chemiluminescent immunoassay (CLIA) for determining of 25-hydroxyvitamin D. Further preferred assays are sandwich fluorescence immunoassay (FIA), Microparticle capture enzyme immunoassay (MEIA), Solid-phase fluorescence immunoassays (SPFIA), Particle concentration fluorescence immunoassay (PCFIA), Nephelometric and Turbidimetric assay with and without latex particle enhancement (LPIA). Also, the assay may be in the form of test strips in an embodiment.

At this time, there are a number of commercially available instruments that utilize electrochemiluminescence (ECL) for analytical measurements. For review see Richter, M. M., Chem. Rev. 104 (2004) 3003-3036. Species that can be induced to emit ECL (ECL-active species) have been used as ECL labels. Examples of ECL labels include organometallic compounds such as the tris-bipyridyl-ruthenium [Ru $(bpy)_3]^{2+}$ moiety where the metal is from, for example, the metals of group VII and VIII, including Re, Ru, Ir and Os. Species that react with the ECL label in the ECL process are referred to herein as ECL coreactants. Commonly used coreactants for ECL include tertiary amines (e.g. tripropylamine (TPA)), oxalate, and persulfate. The light is generated by a concertated reaction of ECL labels and coreactants; the participation of the binding reagent in a binding interaction can be monitored by measuring ECL emitted from the ECL label. Alternatively, the ECL signal from an ECL-active compound may be indicative of the chemical environment (see, e.g., U.S. Pat. Nos. 5,641,623 and 5,643,713, which describes ECL assays that monitor the presence or destruction of special ECL coreactants). For more background on ECL, ECL labels, ECL assays and instrumentation for conducting ECL assays see EP 0 441 875, EP 0 500 305, EP 0 973 035, EP 1 892 524, and published PCT Nos. WO87/06706; WO89/10551; WO90/05301; WO93/01308; WO98/12539; WO99/32662; WO99/58962; WO98/57154 and WO2001/013095.

Commercially available ECL instruments have demonstrated exceptional performance. They have become widely used for reasons including their excellent sensitivity, dynamic range, precision, and tolerance of complex sample matrices. The commercially available instrumentation uses flow cell-based designs with permanent reusable flow cells.

Available sample volumes for the determination of analytes are often limited and more and more different analytes have to be determined out of one sample. Also the development of faster laboratory equipment for assay automation and more sensitive methods for the detection of analytes are required. This leads to the need for high sensitive and specific electrochemiluminescent assays and methods for performing them. In addition improvements associated with safety hazards or environmental concerns should be considered.

In a further embodiment, 25-hydroxyvitamin D is determined in a sandwich assay.

In a further preferred embodiment, a sandwich immunoassay is used in order to determine 25-hydroxyvitamin D in a sample. Such sandwich immunoassay specifically detects 25-hydroxyvitamin D in a sample without interference by 24,25-dihydroxyvitamin $D_3$.

In a sandwich assay the second binding agent according to the present invention is used in an embodiment to capture 25-hydroxyvitamin D and a third binding agent, which is labeled to be directly or indirectly detectable, is used to capture the complex formed of the second binding agent and 25-hydroxyvitamin D.

The second binding agent and the third binding agent used in a sandwich-type assay format are in one embodiment antibodies, respectively or in a further embodiment a combination of a vitamin D-binding protein as second binding agent and an antibody as third binding agent. In case an antibody is used in a sandwich-type assay, also a functionally active part of an antibody may be used in an embodiment.

In one embodiment, the kits of the present invention are used for a qualitative (25-hydroxyvitamin D present or absent) or quantitative (amount of 25-hydroxyvitamin D is determined) or semi-quantitative (relative amounts, in particular above or below a cut-off value are given) immunoassay.

In a preferred embodiment 25-hydroxyvitamin D is detected in an electrochemical or electrochemiluminescence immunoassay (=ECLIA). In an electrochemical or electrochemiluminescent assay a bound analyte molecule is detected by a label linked to a detecting agent (target molecule). An electrode electrochemically initiates luminescence of a chemical label linked to a detecting agent. Light emitted by the label is measured by a photodetector and indicates the presence or quantity of bound analyte molecule/target molecule complexes. ECLA methods are described, for example, in U.S. Pat. Nos. 5,543,112; 5,935,779; and 6,316,607. Signal modulation can be maximized for different analyte molecule concentrations for precise and sensitive measurements.

The term "label" or "detectable label" as used herein refers to any substance that is capable of producing a signal via direct or indirect detection. The detectable label thus may be detected directly or indirectly. For direct detection label suitable for use in the present invention can be selected from any known detectable marker groups, like chromogens, fluorescent groups, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of detectable labels are luminescent metal complexes, such as ruthenium or europium complexes, e.g. as used for ECLIA, enzymes, e.g. as used for ELISA, and radioisotopes; e.g. as used for RIA.

Indirect detection systems comprise, for example, that the detection reagent, e.g. the detection antibody, is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g. by the detectable labels as mentioned above.

The skilled artisan is aware that the first and/or second binding agent may be labelled with a detectable label, respectively. The skilled artisan is aware that the label selected for the first binding agent has to be different from the label selected for the second binding agent.

According to a specific embodiment the first binding agent is mAb<24,25-dihydroxyvitamin $D_3$> and the second binding agent is a vitamin D-binding protein, preferably a labeled vitamin D-binding protein, more preferably a biotinylated or ruthenylated vitamin D-binding protein, respectively.

For direct detection the labeling group or label suitable for use in the present invention can be selected from any known detectable marker groups, but are not limited to, chromogens, fluorescent, chemiluminescent groups (e.g. acridinium esters or dioxetanes), electrochemiluminescent compounds, catalysts, enzymes, enzymatic substrates, dyes, fluorescent dyes (e.g. fluorescein, coumarin, rhodamine, oxazine, resorufin, cyanine and derivatives thereof), colloidal metallic and nonmetallic particles, and organic polymer latex particles. Other examples of labeling groups are luminescent metal complexes, such as ruthenium or europium complexes, enzymes, e.g. as used for ELISA, and radioisotopes.

Indirect detection systems comprise, for example, that the detection reagent, e.g. the detection antibody, is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g. by the labels as mentioned above.

In a specific embodiment, the concentration of 25-hydroxyvitamin D in the sample is of at least 1 nmol/L (0.4 ng/mL), further preferred of at most 500 nmol/L (200 ng/mL), further preferred is in the range of 10 nmol/L (4 ng/mL) to 500 nmol/L (200 ng/mL), further preferred in the range of 10 nmol/L (4 ng/mL) to 250 nmol/L (100 ng/mL).

According to the present invention "crossreact" or "crossreactivity" means, that the binding strength to an vitamin D compound to be determined (e.g. 25-hydroxyvitamin D) distinct from the interfering compound (e.g. 24,25-dihydroxyvitamin $D_3$) against which a first binding agent, in particular an antibody, is directed, has 10% or less, preferably 5% or less of the binding strength measured with the analyte. Binding strength can in particular be measured by applying a affinity test using a BiaCore™. As the skilled artisan knows, the binding affinity (affinity or binding strengths), if given as $K_d$ is the better/higher, the lower the $K_d$.

Moreover, it could be shown in the Examples, that the first binding agent of the invention does not show any significant crossreactivity to 25-hydroxyvitamin D; i.e. the crossreactivity to 25-hydroxyvitamin D has been found to be 10% or less, in particular 5% or less, in particular 1% or less crossreactivity. In an embodiment the first binding agent has no significant crossreactivity to 25-hydroxyvitamin D, preferred the first binding agent has 10% or less crossreactivity to 25-hydroxyvitamin D, further preferred the first binding agent has 5% or less crossreactivity to 25-hydroxyvitamin D, further preferred the first binding agent has 1% or less crossreactivity to 25-hydroxyvitamin D, respectively. Thus, also small amounts of 25-hydroxyvitamin D can be detected specifically and reliably, even in the presence of 24,25-dihydroxyvitamin $D_3$.

According to the present invention, $K_d$(first binding agent) is the affinity of the first binding agent for 24,25-dihydroxyvitamin $D_3$, and $K_d$(second binding agent) is the affinity of the second binding agent for 25-hydroxyvitamin D.

"Affinity" defines the strength of interaction between the two species, and is preferably determined via surface plasmon resonance, in particular using the BiaCore® system. In case of antibodies or antibody fragments, the affinity is determined as $K_d$ value preferably determined via surface plasmon resonance, in particular using the BiaCore® system. The determination of the affinity can be performed as described in "Surface plasmon resonance for detection and measurement of antibody-antigen affinity and kinetics", Current Opinion in Immunology, Volume 5, Issue 2, 1993, Pages 282-286.

Moreover, according to the invention, Conc(first binding agent) and Conc(second binding agent) are the molar concentrations of the first binding agent and the second binding agent, respectively, in step b) of the method of the invention above.

Moreover, according to the invention, MR(first binding agent) is the binding valence of the first binding agent for binding to 24,25-dihydroxyvitamin $D_3$ and MR(second binding agent) is the binding valence of the second binding agent for 25-hydroxyvitamin D.

"Binding valence" according to the present invention is understood as the experimentally determined number of binding sites for a given pair of binding partners. In case of antibodies or functionally active parts thereof, the theoretical binding valence is typically 1 or 2, but experimentally determined binding valences may be non-integer values (e.g. 1.4) due to sterical effects. In case of antibodies as preferred first binding agent, the theoretical binding valence is typically 1. Again, the experimentally determined binding valence may be a non-integer value (e.g. 0.9) due to sterical effects. The determination of the binding valence can be performed as described in Schraeml M. et al. (2012) Methods in Molecular Biology Vol. 901, 171-181.

In order to achieve essentially complete measurement of 25-hydroxyvitamin D, it is advantageous if the $K_d$ of the first binding agent for 24,25-dihydroxyvitamin $D_3$ is at most 10 times higher, preferably the same, more preferably less than the affinity of the second binding agent for 25-hydroxyvitamin D. Therefore, in a further preferred embodiment, $K_d$(first binding agent)/$K_d$(second binding agent) is 10 or less, preferably 1 or less, more preferably 0.1 or less.

In order to achieve essentially complete measurement of 25-hydroxyvitamin D, it is further advantageous in an embodiment if the concentration of the first binding agent is the same, preferably at least 10-fold higher, further preferred 50-fold higher, further preferred 100-fold higher, also preferred 200-fold higher, respectively, than the concentration of the second binding agent. Therefore, in a yet further preferred embodiment, Conc(first binding agent)/Conc(second binding agent) is at most 200, preferably at most 100, preferably at most 50, preferably at most 10, preferably at most 1, respectively, particularly wherein Conc(first binding agent) is in the range of from 1*(1 to 10) nmol/L to 200*(1 to 10) nmol/L, and/or Conc(second binding agent) is in the range of from 1 to 10 nmol/L.

According to a specific embodiment the first binding agent has preferred at least the same, preferably at least 10-times higher, further preferred at least 100-times higher binding affinity to 24,25-dihydroxyvitamin $D_3$, respectively, as the second binding agent.

Another important aspect is the binding valences of the first binding agent and the second binding agent employed in the method of the invention, in particular in case the first binding agent and/or the second binding agent are antibodies or functionally active parts thereof. When binding to small analytes, e.g. a vitamin D compound, a binding molecule being an antibody typically shows a binding valence of MR=2, whereas for sterical reasons, the first binding agent being an antibody typically shows a binding valence of MR=1 and smaller. In this case, the functional molarity quotient is preferably to be considered.

It is further advantageous for determining the total amount of analyte (e.g. a vitamin D compound, preferably 25-hydroxyvitamin D) if the second binding agent, which is intended to bind the analyte, exhibits a sufficiently high affinity to this analyte. Further it is advantageous if the first binding agent, which is intended to bind 24,25-dihydroxyvitamin $D_3$, exhibits a sufficiently high affinity to this 24,25-dihydroxyvitamin $D_3$.

It is further advantageous for determining the total amount of 25-hydroxyvitamin D if the affinity of the first binding agent for binding to 24,25-dihydroxyvitamin $D_3$ is sufficiently high in order to achieve essentially complete binding of 24,25-dihydroxyvitamin $D_3$ to the first binding agent. Therefore in a further embodiment the $K_d$ of the first binding agent for binding to 24,25-dihydroxyvitamin $D_3$ is $10^{-8}$ mol/L or less, preferably $10^{-9}$ mol/L or less, more preferably $10^{-10}$ mol/L or less.

In a yet further embodiment the $K_d$ of the second binding agent for binding to 25-hydroxyvitamin D is $10^{-8}$ mol/L or less, preferably $10^{-9}$ mol/L or less, more preferably $10^{-10}$ mol/L or less.

It is further advantageous if the first binding agent exhibits specificity for the 24,25-dihydroxyvitamin $D_3$ in order to minimize false-positive detection of 25-hydroxyvitamin D. Further, it is advantageous if the first binding agent exhibits specificity for 24,25-dihydroxyvitamin $D_3$, in particular in order to minimize loss of the first binding agent and to maximize binding to 24,25-dihydroxyvitamin $D_3$. Therefore, in a preferred embodiment, the first binding agent binds 24,25-dihydroxyvitamin $D_3$ specifically, in particular binding of the first binding agent to a target different from 24,25-dihydroxyvitamin $D_3$ is at most 5% of the binding of the first binding agent to 24,25-dihydroxyvitamin $D_3$.

In a yet further specific embodiment, the concentration of the first binding agent is in the range of 1*(1 to 10) nmol/L to 200*(1 to 10) nmol/L, such as 1*(1, 2, 3, 4, 5, 6, 7, 8, 9 or 10) nmol/L to 200*(1, 2, 3, 4, 5, 6, 7, 8, 9 or 10) nmol/L, particularly 1 to 1000 nmol/L, 30 to 800 nmol/L, 50 to 700 nmol/L, 100 to 600 nmol/L.

A person skilled in the art is aware that such methods need to be standardized for a quantitative measurement of a vitamin D compound. In a yet further embodiment the methods according to the present invention is standardized by a Vitamin D calibrator.

A person skilled in the art is also aware that the methods for determining the concentration of 25-hydroxyvitamin D without interference by 24,25-dihydroxyvitamin $D_3$ according to the present invention can also be executed with an modified procedure.

In a further embodiment the present invention concerns an in vitro method for determining the concentration of 25-hydroxyvitamin D without interference by 24,25-dihydroxyvitamin $D_3$, the method comprising the steps of:
a) providing a sample obtained from a subject,
b) mixing the sample with a first binding agent binding to 24,25-dihydroxyvitamin $D_3$ and a second binding agent binding to 25-hydroxyvitamin D, thereby forming a first complex between the first binding agent and 24,25-dihydroxyvitamin $D_3$ and a second complex between the second binding agent and 25-hydroxyvitamin D, respectively, and
c) measuring the second complex formed in (b), thereby determining the concentration of 25-hydroxyvitamin D without interference by 24,25-dihydroxyvitamin $D_3$.

In a further embodiment the present invention concerns an in vitro method for determining the concentration of 25-hydroxyvitamin D without interference by 24,25-dihydroxyvitamin $D_3$, the method comprising the steps of:
a) providing a sample obtained from a subject,
b) mixing the sample
ba) with a first binding agent binding to 24,25-dihydroxyvitamin $D_3$, thereby forming a first complex between the first binding agent and 24,25-dihydroxyvitamin $D_3$,
bb) with a second binding agent binding to 25-hydroxyvitamin D, thereby forming a second complex between the binding agent and 25-hydroxyvitamin D,
c) separating the second complex comprising the second binding agent and 25-hydroxyvitamin D from second binding agent not comprising 25-hydroxyvitamin D, and
d) measuring the second complex formed in (bb), thereby measuring 25-hydroxyvitamin D without interference by 24,25-dihydroxyvitamin $D_3$.

In a further embodiment the present invention concerns an in vitro method for determining the concentration of 25-hydroxyvitamin D without interference by 24,25-dihydroxyvitamin $D_3$, the method comprising the steps of:
a) providing a sample obtained from a subject,
b) mixing the sample
(ba) with a first binding agent binding to 24,25-dihydroxyvitamin $D_3$, thereby forming a complex between the first binding agent and 24,25-dihydroxyvitamin $D_3$,
(bb) with a second binding agent binding to 25-hydroxyvitamin D,
c) mixing the sample with a labeled 25-hydroxyvitamin D, the 25-hydroxyvitamin D from the sample and the labeled 25-hydroxyvitamin D competing for binding to the second binding agent binding to 25-hydroxyvitamin D, thereby obtaining a second complex between the second binding agent and the labeled 25-hydroxyvitamin D,
d) separating labeled 25-hydroxyvitamin D comprised in the second complex obtained in step c) from labeled 25-hydroxyvitamin D not comprised in the second complex, and
e) measuring the labeled 25-hydroxyvitamin D comprised in the second complex, thereby measuring 25-hydroxyvitamin D without interference by 24,25-dihydroxyvitamin $D_3$.

In a further embodiment the present invention concerns an in vitro method for determining the concentration of 25-hydroxyvitamin D without interference by 24,25-dihydroxyvitamin $D_3$, the method comprising the steps of:
a) providing a sample obtained from a subject and releasing the vitamin D compound present in the sample bound to vitamin D-binding protein with a release reagent,
b) mixing the sample
(ba) with a first binding agent binding to 24,25-dihydroxyvitamin $D_3$, thereby forming a complex between the first binding agent and 24,25-dihydroxyvitamin $D_3$,
(bb) with a second binding agent binding to 25-hydroxyvitamin D,
c) mixing the sample with a labeled 25-hydroxyvitamin D, the 25-hydroxyvitamin D from the sample and the labeled 25-hydroxyvitamin D competing for binding to the second binding agent binding to 25-hydroxyvitamin D, thereby obtaining a second complex between the second binding agent and the labeled 25-hydroxyvitamin D,
d) separating labeled 25-hydroxyvitamin D comprised in the second complex obtained in step (c) from labeled 25-hydroxyvitamin D not comprised in the second complex, and
e) measuring the labeled 25-hydroxyvitamin D comprised in the second complex, thereby measuring 25-hydroxyvitamin D without interference by 24,25-dihydroxyvitamin $D_3$.

Use:

Using the methods of the invention, the total amount and/or concentration of 25-hydroxyvitamin D may be detected.

In one embodiment the present invention relates to the use of an in vitro method according to the method(s) of the present invention for determining the concentration of 25-hydroxyvitamin D without interference by 24,25-dihydroxyvitamin $D_3$.

In a further embodiment the present invention relates to the use of a first binding agent binding to 24,25-dihydroxyvitamin $D_3$ and a second binding agent binding to 25-hydroxyvitamin D in in vitro method(s) according to the present invention for determining the concentration of 25-hydroxyvitamin D without interference by 24,25-dihydroxyvitamin $D_3$ in a sample obtained from a subject.

Preferably as a first binding agent mAb<24,25-dihydroxyvitamin $D_3$> and as a second binding agent a vitamin D-binding protein is used according to an embodiment of the present invention.

Further the present invention relates in an embodiment to the use of a kit disclosed herein for the determination of 25-hydroxyvitamin D without interference by 24,25-dihydroxyvitamin $D_3$.

Kit:

In one embodiment the present invention relates to a kit for to perform the method(s) according to the present invention comprising at least
a) a first binding agent binding to 24,25-dihydroxyvitamin $D_3$, wherein the first binding agent is an monoclonal antibody or a functionally active part of the monoclonal antibody, and
b) a second binding agent binding to 25-hydroxyvitamin D, wherein the second binding agent is a vitamin D-binding protein.

Preferably as a first binding agent mAb<24,25-dihydroxyvitamin $D_3$> and as a second binding agent a vitamin D-binding protein is provided in a kit according to an embodiment of the present invention.

The skilled artisan is aware that the reagents disclosed herein are suitable for the manufacture of a kit to practice the methods according to the present invention.

In a specific embodiment the kit also comprises a reagent composition which has 0.1 M to 2.0 M of a hydrogen carbonate salt or of a substance capable of releasing hydrogen carbonate ions ($HCO_3^-$) upon hydrolysis, a reducing agent, and an alkalinising agent, preferably the kit comprises a reagent composition which has 0.1 M to 2.0 M of a hydrogen carbonate salt or of a substance capable of releasing hydrogen carbonate ions ($HCO_3^-$) upon hydrolysis, 2 mM to 30 mM of a reducing agent, a solution of 1 M to 1.5 M of an alkalinising agent, in addition to a first binding agent and a second binding agent according to the present invention.

In a further specific embodiment the kit comprises a reducing agent selected from the group consisting of 2-Mercaptoethanol, 2-Mercaptoethylamine-HCl, TCEP, Cystein-HCl and Dithiothreitol (DTT) and a solution of 1 M to 1.5 M of an alkalinising agent selected from the group consisting of NaOH, KOH, $Ca(OH)_2$.

Further the kit comprises in an embodiment a Vitamin D calibrator.

The kit according to the invention has proven to be suitable for use in an automated test for vitamin D compounds. The present invention preferably concerns the use of a kit according to the invention for the determination of 25-hydroxyvitamin D without interference by 24,25-dihydroxyvitamin $D_3$.

The test for 25-hydroxyvitamin D is preferably completely automated. Completely automated in this case means that the experimentator only has to place a sample to be investigated and a reagent pack containing all components for measuring a vitamin D compound on an automated analyzer and all further steps are carried out automatically by the analyzer. The completely automated test is particularly preferably carried out on an Elecsys® analyzer from Roche Diagnostics.

The reagent composition, first binding agent and second binding agent, respectively, according to the invention in a further embodiment are used in an in vitro method for the detection of 25-hydroxyvitamin D without interference by 24,25-dihydroxyvitamin $D_3$, wherein 25-hydroxyvitamin D is selected from the group comprising 25-hydroxyvitamin $D_2$, 25-hydroxyvitamin $D_3$ and 3-epi-25-hydroxyvitamin D, preferably 25-hydroxyvitamin $D_2$, 25-hydroxyvitamin $D_3$.

As already mentioned above 25-hydroxyvitamin $D_2$ and 25-hydroxyvitamin $D_3$ are particularly relevant forms of vitamin D for diagnostics. In the in vitro method(s) according to the invention the specific detection of 25-hydroxyvitamin $D_2$ or 25-hydroxyvitamin $D_3$ or both via a specific antibody to 25-hydroxyvitamin $D_2$ or 25-hydroxyvitamin $D_3$ without interference by 24,25-dihydroxyvitamin $D_3$ also represents a preferred embodiment.

Unless defined otherwise, technical and scientific terms used herein have the same meaning as commonly understood by one of ordinary skill in the art to which this invention belongs.

Singleton et al., Dictionary of Microbiology and Molecular Biology 2nd ed., J. Wiley & Sons, New York, N.Y. (1994); March, Advanced Organic Chemistry Reactions, Mechanisms and Structure, 4th ed., John Wiley & Sons, New York, N.Y. (1992); Lewin, B., Genes V, published by Oxford University Press (1994), ISBN 0-19-854287-9; Kendrew, J. et al. (eds.), The Encyclopedia of Molecular Biology, published by Blackwell Science Ltd. (1994), ISBN 0-632-02182-9; and Meyers, R. A. (ed.), Molecular Biology and Biotechnology: a Comprehensive Desk Reference, published by VCH Publishers, Inc. (1995), ISBN 1-56081-569-8 provide one skilled in the art with a general guide to many of the terms used in the present application.

The practicing of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, Sambrook et al., Molecular Cloning: A Laboratory Manual, second edition (1989); Gait, M. J., Oligonucleotide Synthesis (1984); Freshney, R. I. (ed.), Animal Cell Culture (1987); Methods in Enzymology, Academic Press, Inc.; Ausubel, F. M. et al. (eds.), Current Protocols in Molecular Biology, (1987) and periodic updates; Mullis et al. (eds.), PCR: The Polymerase Chain Reaction (1994).

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments.

Summarizing the findings of the present invention, the following embodiments are preferred:

1. An in vitro method for determining the concentration of 25-hydroxyvitamin D without interference by 24,25-dihydroxyvitamin $D_3$, the method comprising the steps of:
    a) providing a sample obtained from a subject comprising a vitamin D compound bound to vitamin D-binding protein,
    b) mixing the sample
        (ba) with a first binding agent binding to 24,25-dihydroxyvitamin $D_3$, thereby forming a complex between the first binding agent and 24,25-dihydroxyvitamin $D_3$;
        (bb) with a second binding agent binding to 25-hydroxyvitamin D, thereby forming a complex between the second binding agent and 25-hydroxyvitamin D;
    c) measuring the complex formed in (bb), thereby determining the concentration of 25-hydroxyvitamin D without interference by 24,25-dihydroxyvitamin $D_3$.
2. The method according to claim 1, wherein the sample is blood, serum or plasma.
3. The method according to any one of the claims 1 and 2, wherein the vitamin D compound present in the sample bound to vitamin D-binding protein is released from vitamin D-binding protein prior to step (b) with a release reagent.
4. The method according to claim 3, wherein the release reagent denaturates the vitamin D-binding protein, preferably the release reagent irreversible denaturates the vitamin D-binding protein.
5. The method according to any one of the claims 3 and 4, wherein the vitamin D compound is released from the vitamin D-binding protein prior to step (b) by a method selected from the group consisting of a proteolytic degradation, an acidic release, an alkaline release, a methanol release, an ethanol precipitation, a periodate salt release, an acetonitrile extraction, a metal hydroxide release, a release by cyclodextrin and/or derivatives thereof or a metal salicylate release, respectively.

6. The method according to any one of the of claims 3 to 4, wherein the release reagent comprises a hydrogen carbonate salt in a concentration of 0.1 M to 2.0 M and/or a substance capable of releasing hydrogen carbonate ions ($HCO_3^-$) upon hydrolysis in a concentration of 0.1 M to 2.0 M, a reducing agent and an alkalinising agent.

7. The method according to any of the claims 1 to 6, wherein
$K_d$(first binding agent)/$K_d$(second binding agent) is 10 or less, preferably 1 or less, more preferably 0.1 or less; and/or
Conc(first binding agent)/Conc(second binding agent) is at most 200, preferably at most 100, preferably at most 50, more preferably at most 10,
wherein $K_d$(first binding agent) is the affinity of the first binding agent for 24,25-dihydroxyvitamin $D_3$ and $K_d$(second binding agent) is the affinity of the second binding agent for 25-hydroxyvitamin D, and
wherein Conc(first binding agent) and Conc(second binding agent) are the molar concentrations of the first binding agent and the second binding agent, respectively, in step b), particularly wherein Conc(first binding agent) is in the range 1*(1 to 10) nmol/L to 200*(1 to 10) nmol/L, and/or Conc(second binding agent) is in the range of from 1 to 10 nmol/L.

8. The method according to any of the claims 1 to 7, wherein
the $K_d$ of the first binding agent for binding to 24,25-dihydroxyvitamin $D_3$ is $10^{-8}$ mol/L or less, preferably $10^{-9}$ mol/L or less, more preferably $10^{-10}$ mol/L or less; and/or
the $K_d$ of the second binding agent for binding to 25-hydroxyvitamin D is $10^{-8}$ mol/L or less, preferably $10^{-9}$ mol/L or less, more preferably $10^{-10}$ mol/L or less.

9. The method according to any one of the claims 1 to 8,
a) wherein the subject is a human; and/or
b) wherein the method is selected from the group consisting of an enzyme-linked immunoassay (ELISA), electrochemiluminescence immunoassay (ECLIA), radioimmunoassay (RIA) and chemiluminescent immunoassay (CLIA); and/or
c) wherein the 25-hydroxyvitamin D is selected from the group consisting of 25-hydroxyvitamin $D_2$, 25-hydroxyvitamin $D_3$ and 3-epi-25-hydroxyvitamin D; and/or
d) wherein the 25-hydroxyvitamin D is selected from the group consisting of 25-hydroxyvitamin $D_2$ and 25-hydroxyvitamin $D_3$; and/or
e) wherein the first binding agent is selected from the group consisting of polyclonal antibody, monoclonal antibody and synthetic antibody (plastic antibody), preferred a synthetic antibody or monoclonal antibody, further preferred a monoclonal antibody or a functionally active part of the monoclonal antibody, respectively; and/or
f) wherein the second binding agent is a vitamin D-binding protein, preferred a recombinant vitamin D-binding protein; and/or
g) wherein the first binding agent is a monoclonal antibody or a functionally active part of the monoclonal antibody, and the second binding agent is a vitamin D-binding protein or a functionally active part of the vitamin D-binding protein; and/or
h) wherein the first binding agent is mAb<24,25-dihydroxyvitamin $D_3$> and the second binding agent is a vitamin D-binding protein, preferably a labeled vitamin D-binding protein, more preferably a ruthenylated vitamin D-binding protein; and/or
i) wherein the first binding agent is a monoclonal antibody or a functionally active part of the monoclonal antibody and the second binding agent is a monoclonal antibody or a functionally active part of the monoclonal antibody; and/or
j) wherein the first binding agent is mAb<24,25-dihydroxyvitamin $D_3$> or a functionally active part of the monoclonal antibody, and the second binding agent is mAb<25-hydroxyvitamin D> or a functionally active part of the monoclonal antibody, which is capable of immobilizing on a solid support; and/or
k) wherein the first binding agent prevents binding of 24,25-dihydroxyvitamin $D_3$ to the second binding agent; and/or
l) wherein the 24,25-dihydroxyvitamin $D_3$ bound to the first binding agent cannot be bound by the second binding agent; and/or
m) wherein the second binding agent is not capable of releasing the 24,25-dihydroxyvitamin $D_3$ bound to the first binding agent; and/or
n) wherein the first binding agent has at least the same, preferably at least 10-times higher, further preferred at least 100-times higher binding affinity to 24,25-dihydroxyvitamin $D_3$, respectively, as the second binding agent; and/or
o) wherein the first binding agent has no significant crossreactivity to 25-hydroxyvitamin D, preferred the first binding agent has 10% or less crossreactivity to 25-hydroxyvitamin D, further preferred the first binding agent has 5% or less crossreactivity to 25-hydroxyvitamin D, further preferred the first binding agent has 1% or less crossreactivity to 25-hydroxyvitamin D, respectively; and/or
p) wherein the first binding agent and the second binding agent according to step (b) of claim 1 are contacted simultaneously with the sample; and/or
q) wherein the first binding agent is contacted with the sample according to step b) of claim 1 before or after contacting the second binding agent with the sample; and/or
r) wherein the concentration of 25-hydroxyvitamin D in the sample is of at least at least 1 nmol/L (0.4 ng/mL), further preferred of at most 500 nmol/L (200 ng/mL), further preferred is in the range of 10 nmol/L (4 ng/mL) to 500 nmol/L (200 ng/mL), further preferred in the range of 10 nmol/L (4 ng/mL) to 250 nmol/L (100 ng/mL); and/or
s) wherein the method is standardized by a Vitamin D calibrator.

10. Use of an in vitro method according to any one of the claims 1 to 9 for determining the concentration of 25-hydroxyvitamin D without interference by 24,25-dihydroxyvitamin $D_3$.

11. Use of a first binding agent binding to 24,25-dihydroxyvitamin $D_3$ and a second binding agent binding to 25-hydroxyvitamin D in an in vitro method for determining the concentration of 25-hydroxyvitamin D without interference by 24,25-dihydroxyvitamin $D_3$ in a sample obtained from a subject.

12. A kit to perform the method according to any one of the claims 1 to 9 comprising at least
   a) a first binding agent binding to 24,25-dihydroxyvitamin $D_3$, wherein the first binding agent is an monoclonal antibody or a functionally active part of the monoclonal antibody, and
   b) a second binding agent binding to 25-hydroxyvitamin D, wherein the second binding agent is a vitamin D-binding protein.

13. An in vitro method for determining the concentration of 25-hydroxyvitamin D without interference by 24,25-dihydroxyvitamin $D_3$, the method comprising the steps of:
   a) providing a sample obtained from a subject,
   b) mixing the sample with a first binding agent binding to 24,25-dihydroxyvitamin $D_3$ and a second binding agent binding to 25-hydroxyvitamin D, thereby forming a first complex between the first binding agent and 24,25-dihydroxyvitamin $D_3$ and a second complex between the second binding agent and 25-hydroxyvitamin D, respectively, and
   c) measuring the second complex formed in (b), thereby determining the concentration of 25-hydroxyvitamin D without interference by 24,25-dihydroxyvitamin $D_3$.

14. An in vitro method for determining the concentration of 25-hydroxyvitamin D without interference by 24,25-dihydroxyvitamin $D_3$, the method comprising the steps of:
   a) providing a sample obtained from a subject,
   b) mixing the sample
      ba) with a first binding agent binding to 24,25-dihydroxyvitamin $D_3$, thereby forming a first complex between the first binding agent and 24,25-dihydroxyvitamin $D_3$,
      bb) with a second binding agent binding to 25-hydroxyvitamin D, thereby forming a second complex between the binding agent and 25-hydroxyvitamin D,
   c) separating the second complex comprising the second binding agent and 25-hydroxyvitamin D from second binding agent not comprising 25-hydroxyvitamin D, and
   d) measuring the second complex formed in (bb), thereby measuring 25-hydroxyvitamin D without interference by 24,25-dihydroxyvitamin $D_3$.

15. An in vitro method for determining the concentration of 25-hydroxyvitamin D without interference by 24,25-dihydroxyvitamin $D_3$, the method comprising the steps of:
   a) providing a sample obtained from a subject,
   b) mixing the sample
      (ba) with a first binding agent binding to 24,25-dihydroxyvitamin $D_3$, thereby forming a complex between the first binding agent and 24,25-dihydroxyvitamin $D_3$,
      (bb) with a second binding agent binding to 25-hydroxyvitamin D,
   c) mixing the sample with a labeled 25-hydroxyvitamin D, the 25-hydroxyvitamin D from the sample and the labeled 25-hydroxyvitamin D competing for binding to the second binding agent binding to 25-hydroxyvitamin D, thereby obtaining a second complex between the second binding agent and the labeled 25-hydroxyvitamin D,
   d) separating labeled 25-hydroxyvitamin D comprised in the second complex obtained in step (c) from labeled 25-hydroxyvitamin D not comprised in the second complex, and
   e) measuring the labeled 25-hydroxyvitamin D comprised in the second complex, thereby measuring 25-hydroxyvitamin D without interference by 24,25-dihydroxyvitamin $D_3$.

16. An in vitro method for determining the concentration of 25-hydroxyvitamin D without interference by 24,25-dihydroxyvitamin $D_3$, the method comprising the steps of:
   a) providing a sample obtained from a subject and releasing the vitamin D compound present in the sample bound to vitamin D-binding protein with a release reagent,
   b) mixing the sample
      (ba) with a first binding agent binding to 24,25-dihydroxyvitamin $D_3$, thereby forming a complex between the first binding agent and 24,25-dihydroxyvitamin $D_3$,
      (bb) with a second binding agent binding to 25-hydroxyvitamin D,
   c) mixing the sample with a labeled 25-hydroxyvitamin D, the 25-hydroxyvitamin D from the sample and the labeled 25-hydroxy vitamin D competing for binding to the second binding agent binding to 25-hydroxyvitamin D, thereby obtaining a second complex between the second binding agent and the labeled 25-hydroxyvitamin D,
   d) separating labeled 25-hydroxyvitamin D comprised in the second complex obtained in step (c) from labeled 25-hydroxyvitamin D not comprised in the second complex, and
   e) measuring the labeled 25-hydroxyvitamin D comprised in the second complex, thereby measuring 25-hydroxyvitamin D without interference by 24,25-dihydroxyvitamin $D_3$.

Example 1

Procedures for Synthesis of a Blocking Reagent for 24,25-Dihydroxyvitamin $D_3$ 1.1 Synthesis of Antigen and Antigen Conjugate Synthesis of 7-{2-[2-(2-{(S)-3-[2-[(1R,7aR)-1-((R)-4,5-Dihydroxy-1,5-dimethyl-hexyl)-7a-methyl-octahydro-inden-(4E)-ylidene]-eth-(Z)-ylidene]-4-methylene-cyclohexyloxycarbonylamino}-ethoxy)-ethoxy]-ethylcarbamoyl}-heptanoic acid N-hydroxysuccinimide ester (NHS ester of acid in FIG. 1)

The synthesis of the starting material 24,25-O-isopropyliden-24R, 25-dihydroxyvitamin $D_3$ is described by Sestelo, Jose Perez; Cornella, Ivan; De Una, Olga; Mourino, Antonio; Sarandeses, Luis A., Chemistry—A European Journal (2002), 8(12), 2747-2752. The structure is shown in FIG. 1.

100 mg of the starting material and 26.8 mg of DMAP was dried in a flask and 20 ml of dichloromethane was added. After the addition of 121 µl triethylamine 86.7 mg phosgene as toluene 20% solution was added. The solution was stirred for 45 minutes under inert atmosphere and protected from light at room temperature (RT; RT is known to the person skilled in the art as 20° C. to 25° C. (68° F. to 77° F.) and 324.6 mg of diamino-dioxa-octane dissolved in 10 ml dichloromethane was added. The mixture was further stirred overnight under the same condition. The product was purified by preparative HPLC. Yield=72 mg.

55 mg of the amine derivative was converted to the NHS ester by reacting with 168 mg octanedioic acid bis N-hydroxysuccinimide ester, 68 µl triethylamine in acetonitrile overnight at room temperature (RT). The protecting group was cleaved by addition of around 1 g Dowex 50WXH and continuously stirring until the reaction was completed. The product was purified by preparative HPLC. Yield 16 mg. HPLC-ESI-MS: M$^+$=844.7 Da Synthesis of Antigen Conjugate:

5.63 mg of the NHS ester described above was dissolved in 500 µl DMSO and added to a solution of 50 mg KLH (Keyhole Limpet Hemocyanin, Sigma H 8283). The pH was adjusted to pH=8.3 and the solution stirred overnight. The mixture was purified in an Amicon stirred cell.

Analytics of Amino Groups: Antigen-KLH Ratio App. 500:1

1.2 Generation of Antibodies Against 24,25-Dihydroxyvitamin $D_3$

Antibody Development with Rabbit B-Cell PCR:

For the generation of antibodies against 24,25-dihydroxyvitamin $D_3$ 16-week old ZiKa rabbits were immunized with 24,25-dihydroxyvitamin $D_3$ coupled to KLH. All rabbits were subjected to repeated immunizations. In the first months the animals were immunized weekly. From the second month onward the animals were immunized once per month. For each immunization 500 µg KLH-coupled 24,25-dihydroxyvitamin $D_3$ was dissolved in 1 mL 140 mM NaCl and was emulsified in 1 ml CFA. The development of titers is evaluated on days 45 and 105 after start of the immunization. When titers against the immunogen are detectable by ELISA, antibodies are developed by B-cell cloning as described in Seeber et al. 2014. Recombinant full-length rabbit IgG is produced by transient transfection of HEK293 cells.

Titer Analysis:

For the determination of the serum titers against 24,25-dihydroxyvitamin $D_3$ a biotinylated variant of 24,25-dihydroxyvitamin $D_3$ was coupled to Streptavidin coated 96-well plates. A small amount of serum of each rabbit is collected on day 45 and day 105 after start of the immunization campaign. Biotinylated 24,25-dihydroxyvitamin $D_3$ was immobilized on the plate surface at a concentration of 15 ng/mL. The sera from each rabbit were diluted in PBS with 1% BSA and the dilutions were added to the plates. The sera were tested at dilutions 1:300, 1:900, 1:2700, 1:8100, 1:24300, 1:72900, 1:218700 and 1:656100. Bound antibody was detected with a HRP-labeled F(ab')$_2$ goat anti-rabbit Fcγ (Dianova) and ABTS (Roche) as a substrate.

Example 2

Applying a Blocking Reagent for 24,25-Dihydroxyvitamin $D_3$ to a Binding Assay

Depending on the assay procedure a blocking reagent (e.g. a polyclonal antibody, a monoclonal antibody, a functionally active part of a monoclonal antibody, or a synthetic antibody (plastic antibody)) that specifically binds 24,25-dihydroxyvitamin $D_3$ can be added to pretreatment or releasing reagents, assay diluents or assay buffers bringing them in contact with vitamin D compounds in a sample before or together with the respective labeled binding component (conjugate) of the assay.

Figure 2A:
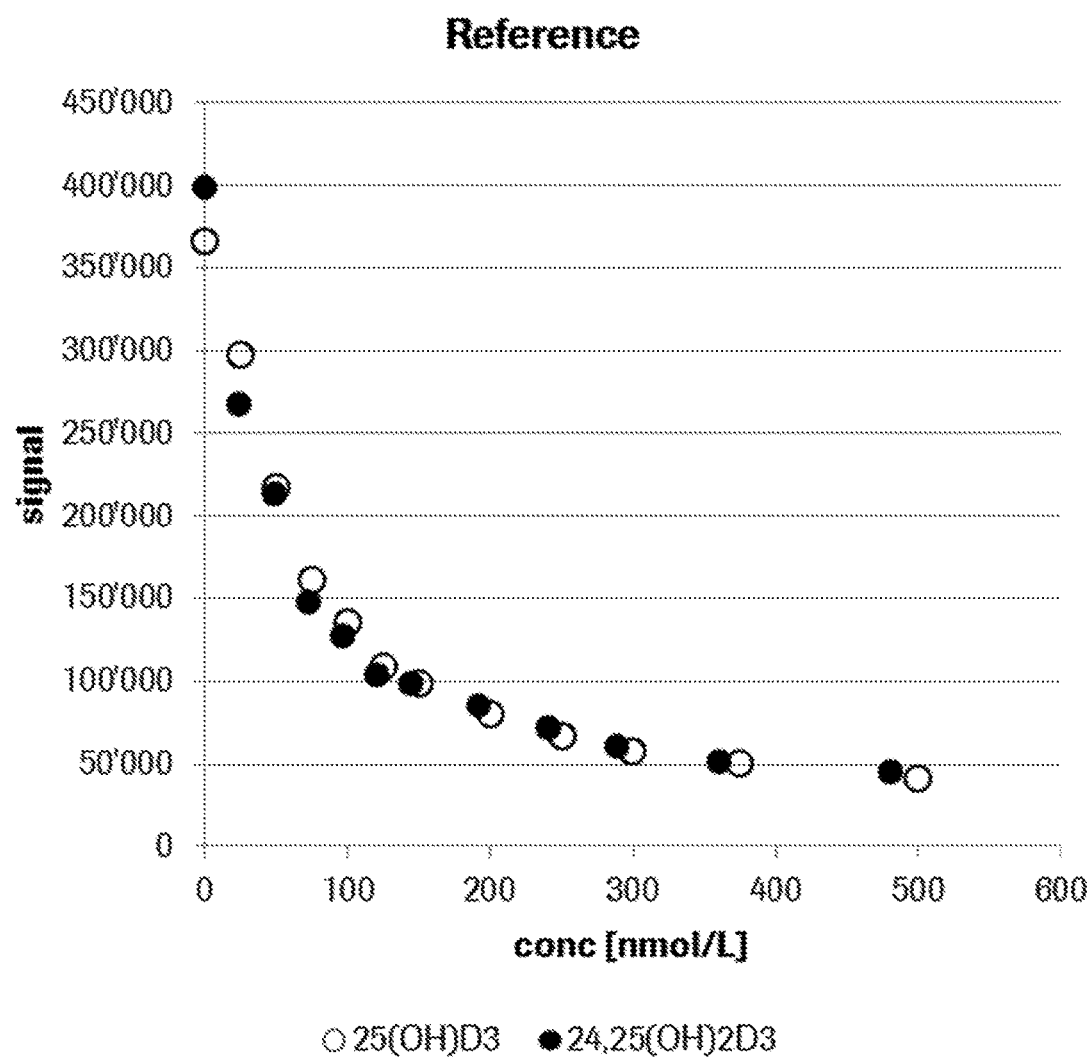
FIG. 2A.
Figure 2B:
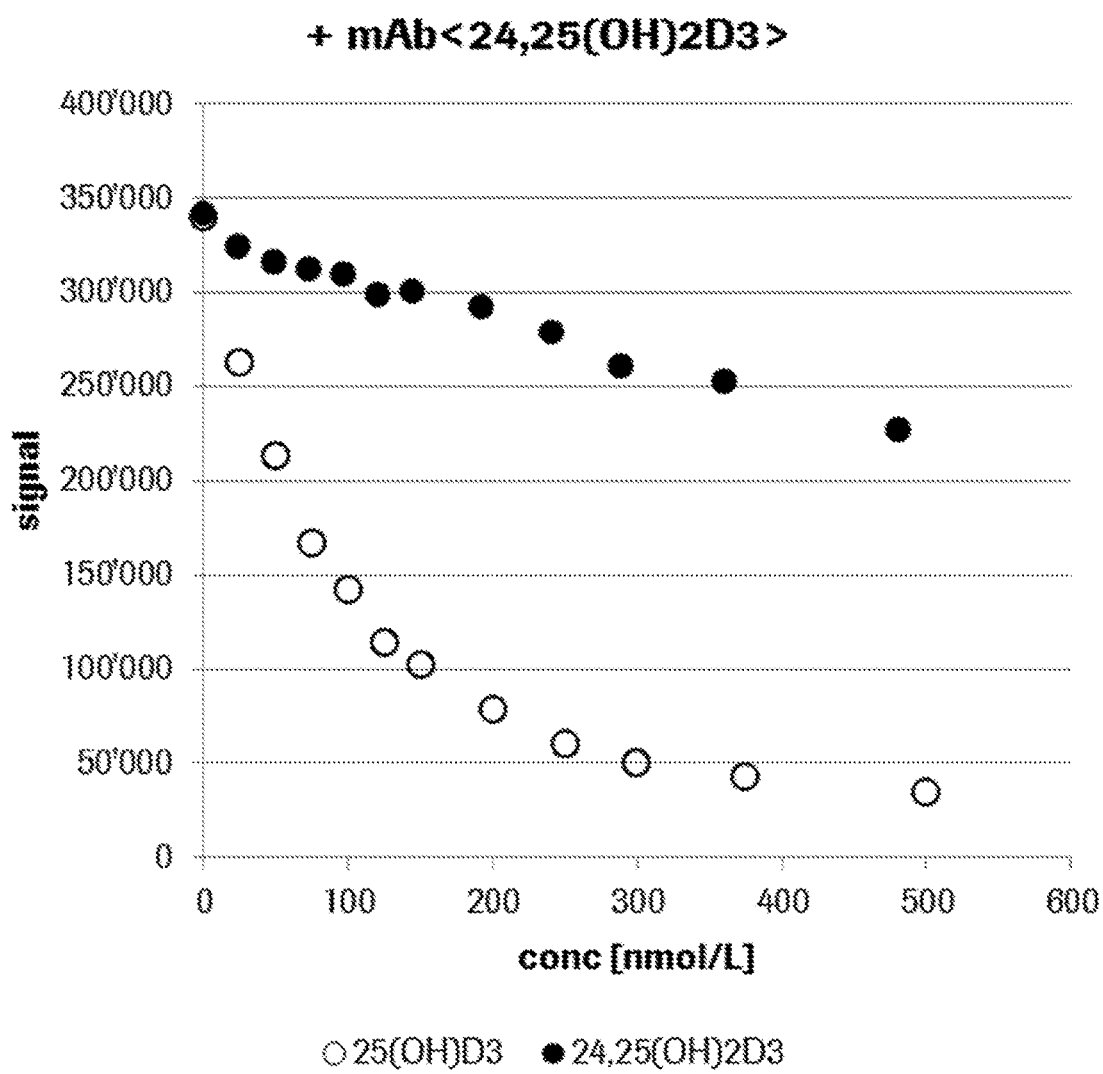
FIG. 2B.

As an example the blocking of 24,25-dihydroxyvitamin $D_3$ in the Elecsys® Vitamin D total immunoassay is described:

- 0.075 mg/mL of mAb<24,25-dihydroxyvitamin $D_3$>rK-IgG were added to reagent R1 of the Elecsys® Vitamin D total immunoassay containing the ruthenylated Vitamin D-binding protein conjugate.
- The Vitamin D total assay application was run with dilution series of either 25-hydroxyvitamin $D_3$ (○, 25(OH)$D_3$) or 24,25-dihydroxyvitamin $D_3$ (●, 24,25 (OH)2D3) in a matrix free of vitamin D metabolites (Diluent Universal)
- The reference (without blocking reagent) showed cross-reactivity to 25-hydroxyvitamin $D_3$ and 24,25-dihydroxyvitamin $D_3$ (Table 1 and FIG. 2a)
- The immunoassay application with blocking reagent showed reduced cross-reactivity to 24,25-dihydroxyvitamin $D_3$ while the specificity for 25-hydroxyvitamin $D_3$ is not affected (Table 1 and FIG. 2b)

TABLE 1

The effect of mAb<24,25-dihydroxyvitamin $D_3$>rK-IgG on signal dynamics (shown as B/B0) for 25-hydroxyvitamin $D_3$ (25(OH)$D_3$) and 24,25-dihydroxyvitamin $D_3$ (24,25(OH)2D3).

|  |  | Reference ○ | | mAb<24,25(OH)2VitD3> ● | |
| --- | --- | --- | --- | --- | --- |
|  |  | Signal (mean) | B/B0 | Signal (mean) | B/B0 |
| 25(OH)VitD3 | 0 nmoL/L | 366'500 |  | 340'300 |  |
|  | 25 nmoL/L | 297'200 | 81% | 262'400 | 77% |
|  | 50 nmoL/L | 217'500 | 59% | 214'000 | 63% |
|  | 75 nmoL/L | 161'600 | 44% | 167'500 | 49% |
|  | 100 nmoL/L | 135'600 | 37% | 142'700 | 42% |
|  | 125 nmoL/L | 108'900 | 30% | 113'900 | 33% |
|  | 150 nmoL/L | 98'860 | 27% | 102'500 | 30% |
|  | 200 nmoL/L | 79'820 | 22% | 78'620 | 23% |
|  | 250 nmoL/L | 67'020 | 18% | 60'020 | 18% |
|  | 300 nmoL/L | 58'210 | 16% | 50'500 | 15% |
|  | 374 nmoL/L | 50'550 | 14% | 42'740 | 13% |
|  | 499 nmoL/L | 41'190 | 11% | 34'610 | 10% |
| 24,25(OH)2VitD3 | 0 nmoL/L | 399'400 |  | 342'100 |  |
|  | 24 nmoL/L | 268'100 | 67% | 325'200 | 95% |
|  | 48 nmoL/L | 213'600 | 53% | 316'400 | 92% |
|  | 72 nmoL/L | 147'700 | 37% | 313'000 | 91% |
|  | 96 nmoL/L | 127'300 | 32% | 309'900 | 91% |
|  | 120 nmoL/L | 103'700 | 26% | 299'600 | 88% |
|  | 144 nmoL/L | 98'420 | 25% | 301'200 | 88% |
|  | 192 nmoL/L | 85'250 | 21% | 292'900 | 86% |

TABLE 1-continued

The effect of mAb<24,25-dihydroxyvitamin D$_3$>rK-IgG on signal dynamics (shown as B/B0) for 25-hydroxyvitamin D$_3$ (25(OH)D$_3$) and 24,25-dihydroxyvitamin D$_3$ (24,25(OH)2D3).

|  | Reference ○ | | mAb<24,25(OH)2VitD3> ● | |
|---|---|---|---|---|
|  | Signal (mean) | B/B0 | Signal (mean) | B/B0 |
| 240 nmoL/L | 71'560 | 18% | 279'100 | 82% |
| 288 nmoL/L | 61'070 | 15% | 260'900 | 76% |
| 360 nmoL/L | 51'180 | 13% | 252'300 | 74% |
| 480 nmoL/L | 45'010 | 11% | 227'300 | 66% |

Figure 3A:
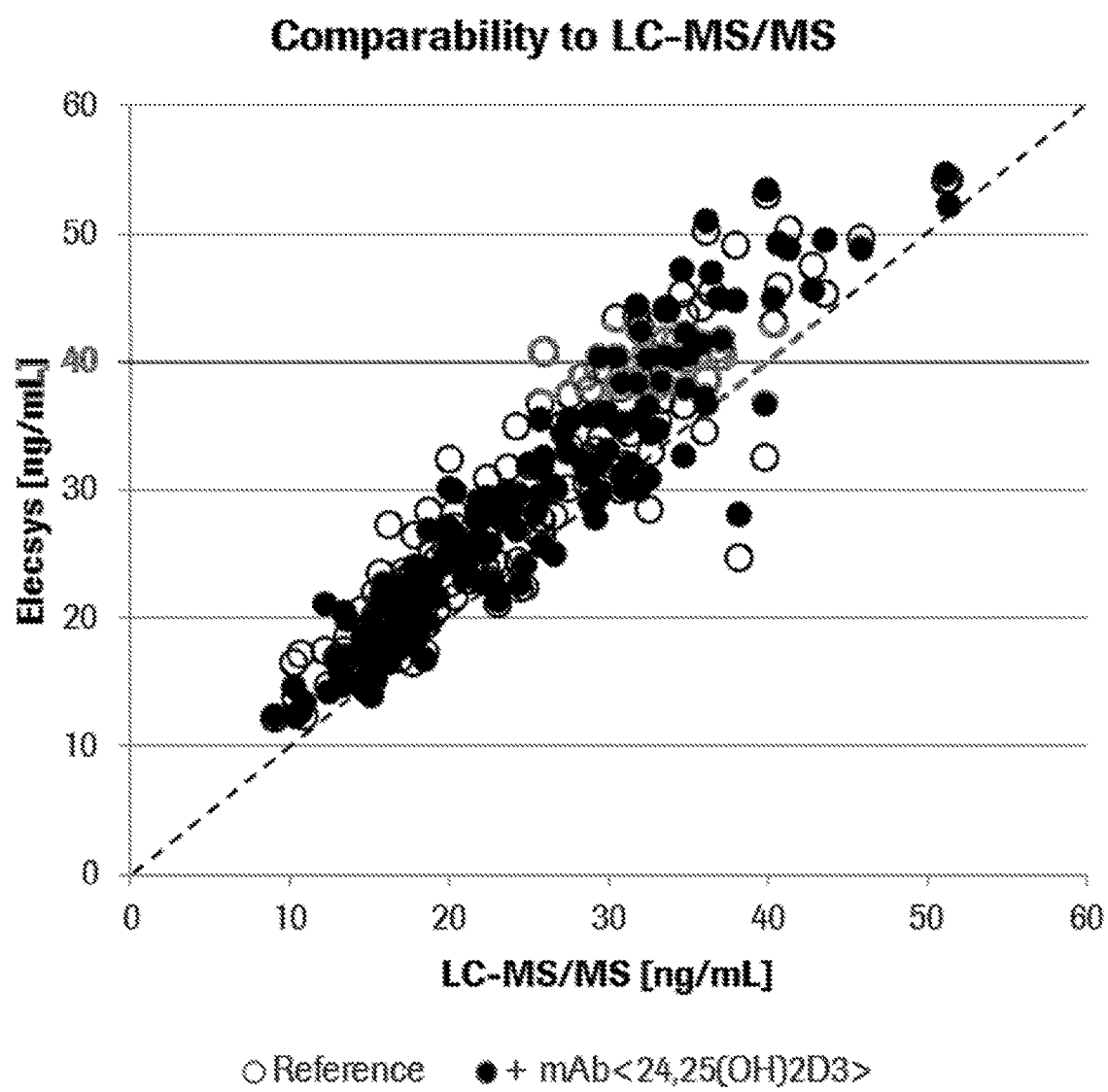
FIG. 3A: The correlation between Elecsys® Vitamin D total immunoassay and LC-MS vitamin D measurements is shown in FIG. 3a for a sample set. Without blocking reagent (○, without first binding agent) and with blocking agent (●, with first binding agent).
Figure 3B:
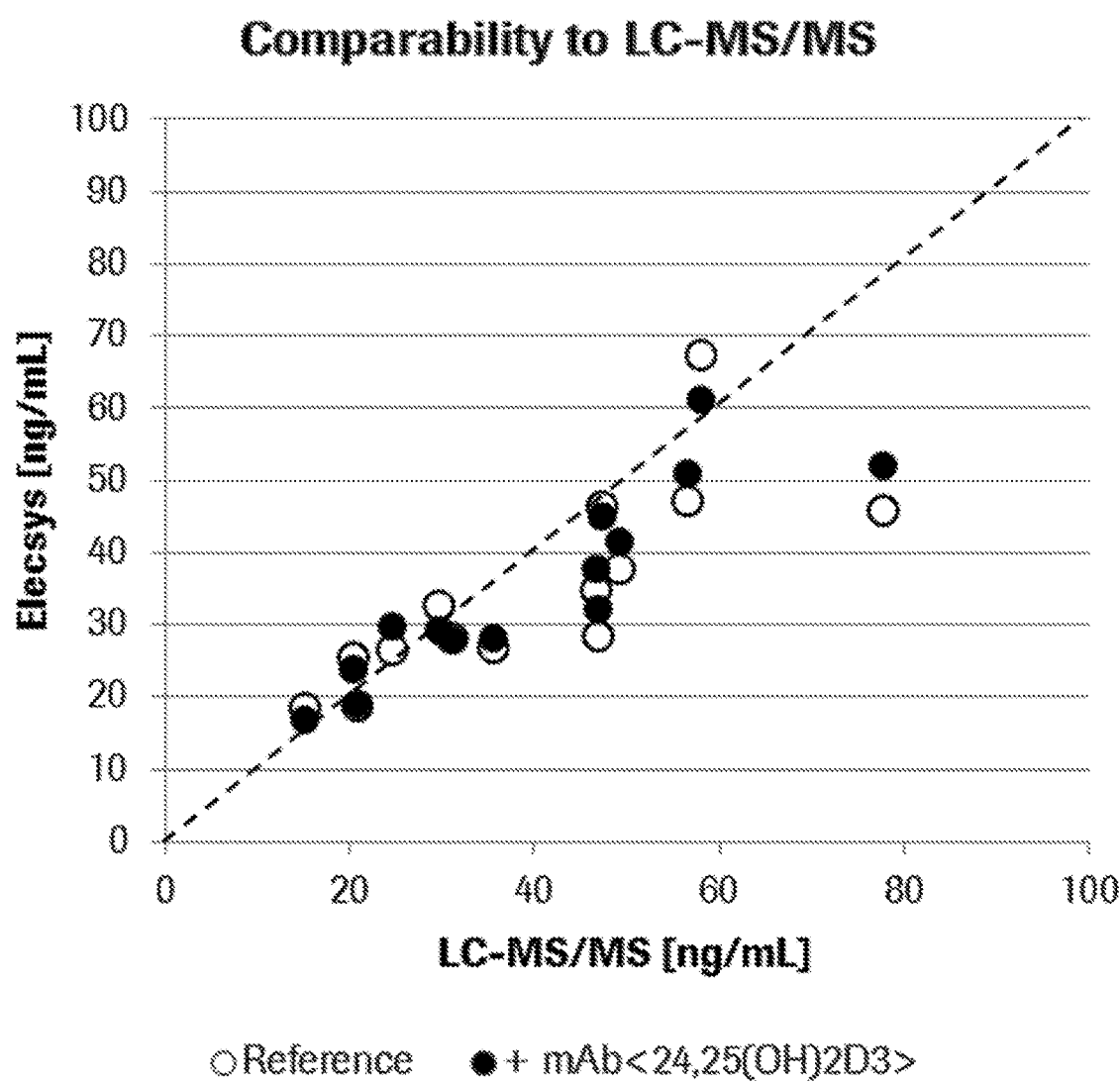
FIG. 3B: The correlation between Elecsys® Vitamin D total immunoassay and LC-MS vitamin D measurements is shown in FIG. 3a for another sample set. Without blocking reagent (○, without first binding agent) and with blocking agent (●, with first binding agent).

The positive effect of the mAb<24,25-dihydroxyvitamin D$_3$>rK-IgG could also be seen independently for two different sample sets in the improved correlation to LC-MS/MS which is specific for 25-hydroxyvitamin D$_2$ and 25-hydroxyvitamin D$_3$ only (FIGS. 3a and 3b). Without blocking agent (○) the correlation is 0.92 (left) or 0.79 (right). After adding the mAb<24,25-dihydroxyvitamin D$_3$>rK-IgG (●, mAb<24,25(OH)2D3>) the correlation improved to 0.94 (left) or 0.90 (right), respectively.

The invention claimed is:

1. An in vitro method for determining the concentration of 25-hydroxyvitamin D without interference by 24,25-dihydroxyvitamin D3, the method comprising the steps of:
   a) providing a sample obtained from a subject comprising a vitamin D compound bound to vitamin D-binding protein,
   b) mixing the sample (1) with a first binding agent binding to 24,25-dihydroxyvitamin D3, thereby forming a complex between the first binding agent and 24,25-dihydroxyvitamin D3; (2) with a second binding agent binding to 25-hydroxyvitamin D, thereby forming a complex between the second binding agent and 25-hydroxyvitamin D, wherein K$_d$(first binding agent)/K$_d$(second binding agent) is 10 or less, wherein K$_d$(first binding agent) is the affinity of the first binding agent for 24,25-dihydroxyvitamin D3 and K$_d$(second binding agent) is the affinity of the second binding agent for 25-hydroxyvitamin D3, and wherein the first binding agent blocks binding of 24,25-dihydroxyvitamin D3 to the second binding agent; and
   c) measuring the complex formed in (b2), thereby determining the concentration of 25-hydroxyvitamin D without interference by 24,25-dihydroxyvitamin D3, wherein the first and second binding agents are different antibodies, wherein the sample is mixed with the first binding agent before mixing the sample with the second binding agent and wherein the first binding agent has no significant crossreactivity to 25-hydroxyvitamin D.

2. The method according to claim 1, wherein the sample is blood, serum or plasma.

3. The method according to claim 1, wherein the vitamin D compound present in the sample bound to vitamin D-binding protein is released from vitamin D-binding protein prior to step (b) with a release reagent.

4. The method according to claim 1, wherein
Conc(first binding agent)/Conc(second binding agent) is at most 200;
wherein Conc(first binding agent) and Conc(second binding agent) are the molar concentrations of the first binding agent and the second binding agent, respectively, in step b).

5. The method according to claim 1, wherein
the K$_d$ of the first binding agent for binding to 24,25-dihydroxyvitamin D$_3$ is 10$^{-8}$ mol/L or less; and/or the K$_d$ of the second binding agent for binding to 25-hydroxyvitamin D is 10$^{-8}$ mol/L or less.

6. The method according to claim 1, wherein the method is selected from the group consisting of an enzyme-linked immunoassay (ELISA), electrochemiluminescence immunoassay (ECLIA), radioimmunoassay (RIA) and chemiluminescent immunoassay (CLIA).

7. The method according to claim 1, wherein the 25-hydroxyvitamin D is selected from the group consisting of 25-hydroxyvitamin D$_2$, 25-hydroxyvitamin D$_3$ and 3-epi-25-hydroxyvitamin D.

8. The method according to claim 1, wherein the second binding agent is not capable of releasing the 24,25-dihydroxyvitamin D$_3$ bound to the first binding agent.

9. The method according to claim 1, wherein the in vitro method of detection is carried out as a competitive assay.

10. The method according to claim 1, wherein Conc(first binding agent) is in the range 1×(1 to 10) nmol/L to 200×(1 to 10) nmol/L, and/or Conc(second binding agent) is in the range of from 1 to 10 nmol/L.

11. The method according to claim 1, wherein the first binding agent is a monoclonal antibody binding to 24,25-dihydroxyvitamin D3 or a functionally active part of the monoclonal antibody and the second binding agent is a monoclonal antibody binding to 25-hydroxyvitamin D or a functionally active part of the monoclonal antibody.

12. The method according to claim 1, wherein the first binding agent is a monoclonal antibody binding to 24,25-dihydroxyvitamin D3 or a functionally active part of the monoclonal antibody.

13. The method according to claim 1, wherein the first binding agent has at least 10-times higher binding affinity to 24,25-dihydroxyvitamin D3 as the second binding agent.

14. The method according to claim 1, wherein the first binding agent has 10% or less crossreactivity to 25-hydroxyvitamin D.

* * * * *